United States Patent
Lee et al.

(10) Patent No.: US 12,144,598 B2
(45) Date of Patent: Nov. 19, 2024

(54) SYSTEMS AND METHODS FOR REVASCULARIZATION ASSESSMENT

(71) Applicant: Nanyang Technological University, Singapore (SG)

(72) Inventors: Kijoon Lee, Singapore (SG); Renzhe Bi, Singapore (SG); Jing Dong, Singapore (SG); Justin Dauwels, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 17/808,956

(22) Filed: Jun. 24, 2022

(65) Prior Publication Data

US 2023/0148888 A1    May 18, 2023

Related U.S. Application Data

(63) Continuation of application No. 16/400,668, filed on May 1, 2019, now abandoned, which is a continuation of application No. 15/892,300, filed on Feb. 8, 2018, now abandoned, which is a continuation of application No. 15/377,864, filed on Dec. 13, 2016, now abandoned, which is a continuation of application No. 14/460,231, filed on Aug. 14, 2014, now abandoned.

(60) Provisional application No. 61/888,790, filed on Oct. 9, 2013, provisional application No. 61/865,977, filed on Aug. 14, 2013.

(51) Int. Cl.
| | |
|---|---|
| *A61B 5/00* | (2006.01) |
| *A61B 5/02* | (2006.01) |
| *A61B 5/026* | (2006.01) |
| *G16H 50/20* | (2018.01) |
| *A61B 5/0265* | (2006.01) |

(52) U.S. Cl.
CPC ........ *A61B 5/0261* (2013.01); *A61B 5/02007* (2013.01); *A61B 5/6829* (2013.01); *G16H 50/20* (2018.01); *A61B 5/0075* (2013.01); *A61B 5/0265* (2013.01); *A61B 5/6831* (2013.01); *A61B 5/7246* (2013.01); *A61B 5/7257* (2013.01); *A61B 5/726* (2013.01); *A61B 5/7282* (2013.01)

(58) Field of Classification Search
None
See application file for complete search history.

(56) References Cited

PUBLICATIONS

Renzhe Bi, Jing Dong, and Kijoon Lee, "Deep tissue flowmetry based on diffuse speckle contrast analysis," Opt. Lett. 38, 1401-1403 (Year: 2013).*

(Continued)

*Primary Examiner* — Pascal M Bui Pho
*Assistant Examiner* — Michael S Kellogg
(74) *Attorney, Agent, or Firm* — KNOBBE MARTENS OLSON & BEAR LLP

(57) ABSTRACT

Disclosed herein are systems and methods for revascularization assessment. The methods can in some cases include one or more of the steps of measuring blood perfusion as a function of time to obtain time series data, mathematically transforming the time series data into a power spectrum, calculating at least one parameter of the power spectrum within a specific frequency range, and using the at least one calculated parameter as a discriminator for the first population and the second population.

6 Claims, 29 Drawing Sheets

(56) References Cited

PUBLICATIONS

Dunn AK, Bolay H, Moskowitz MA, Boas DA. Dynamic Imaging of Cerebral Blood Flow Using Laser Speckle. Journal of Cerebral Blood Flow & Metabolism.;21(3):195-201. doi:10.1097/00004647-200103000-00002 (Year: 2001).*

* cited by examiner

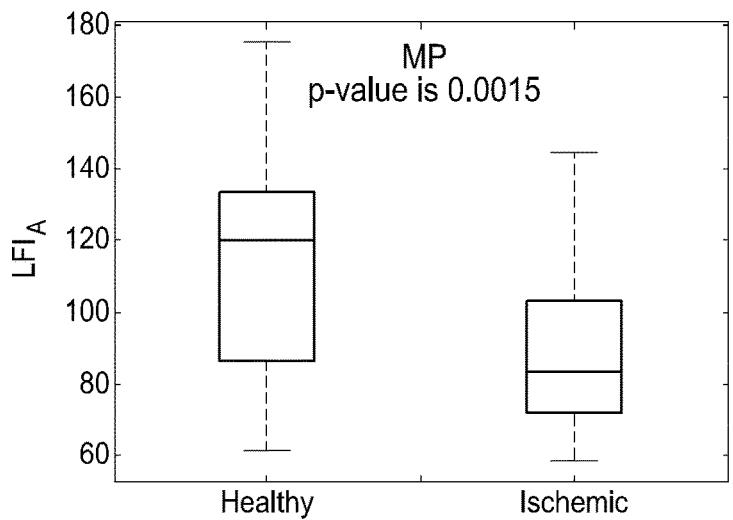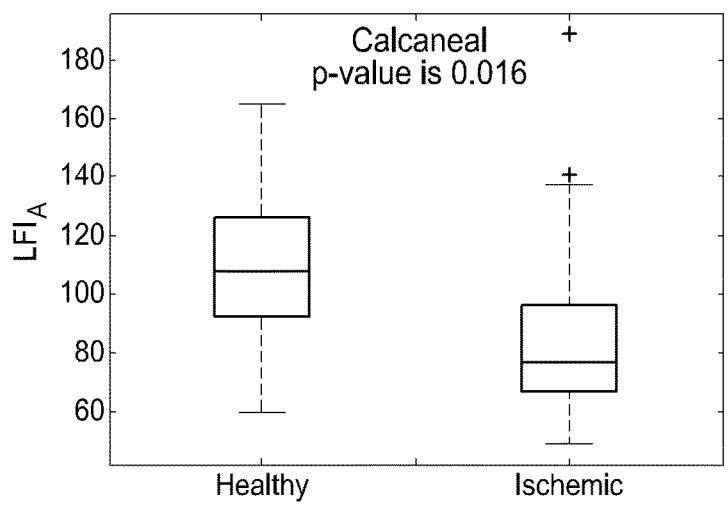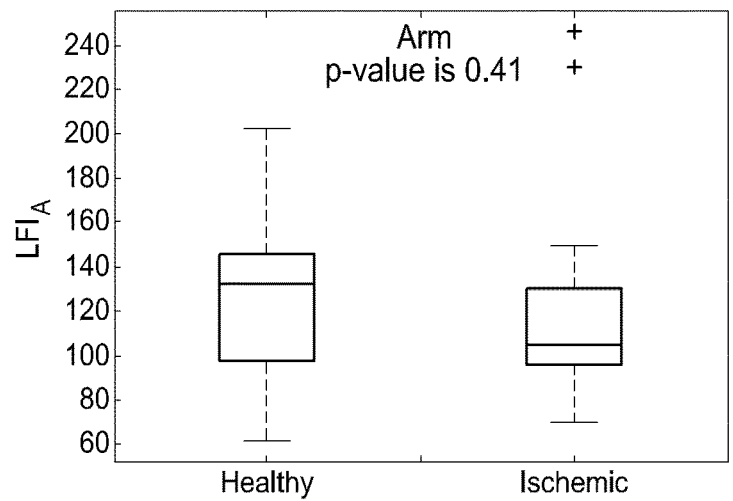
FIG. 9B

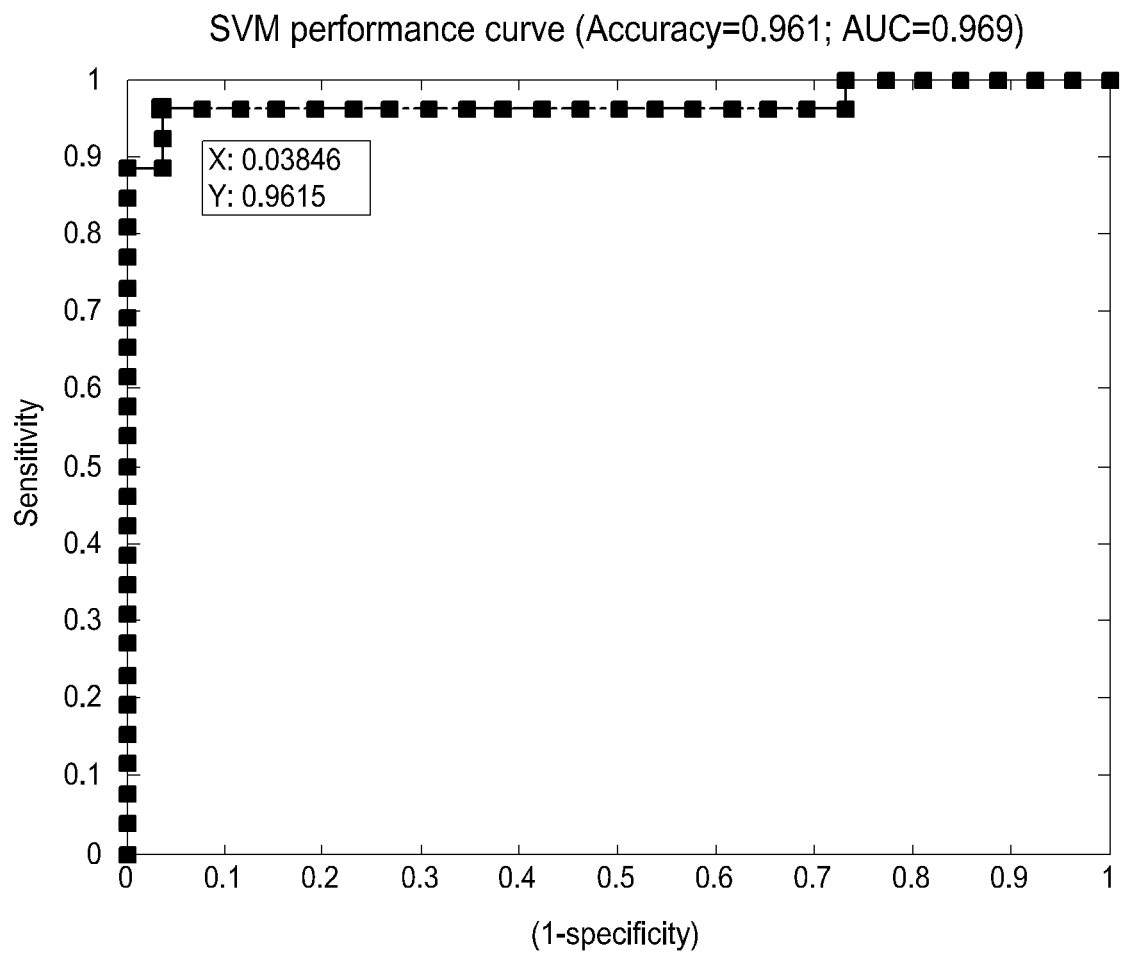
FIG. II

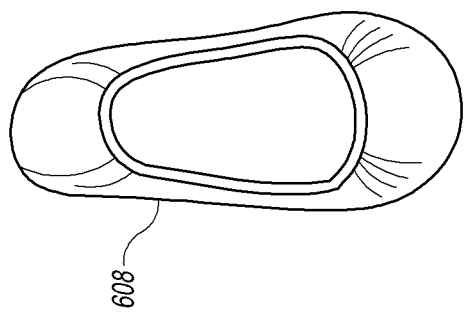
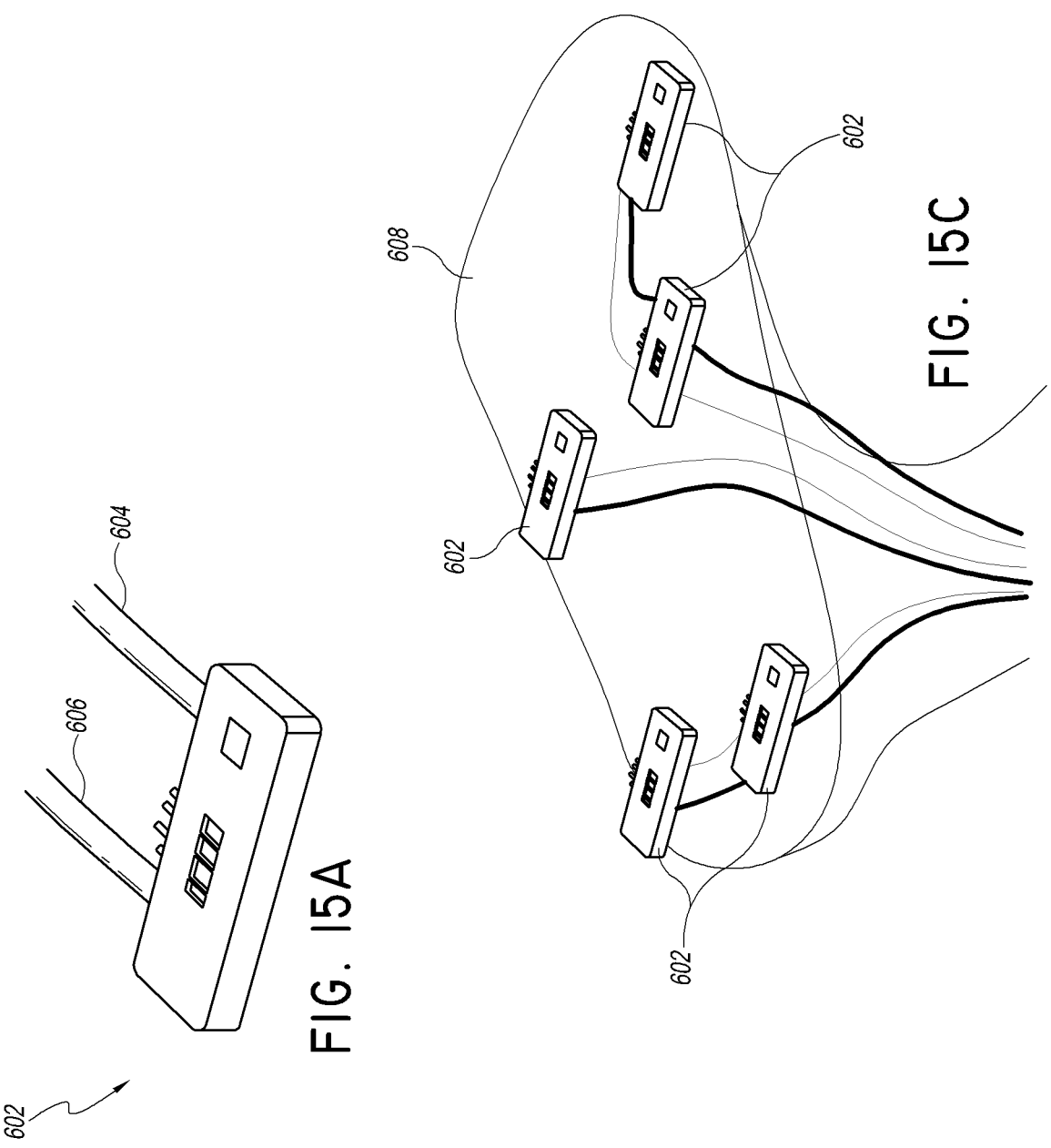

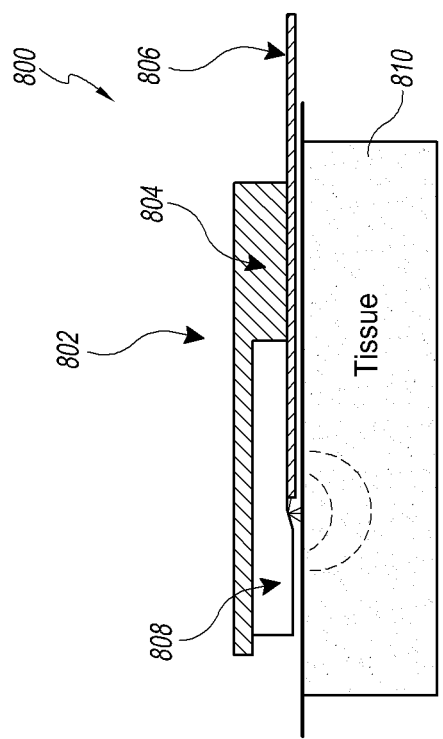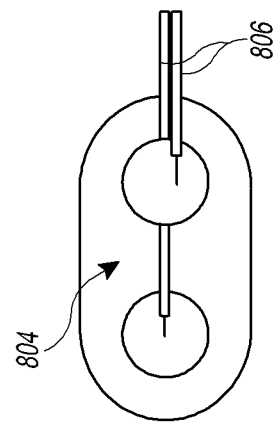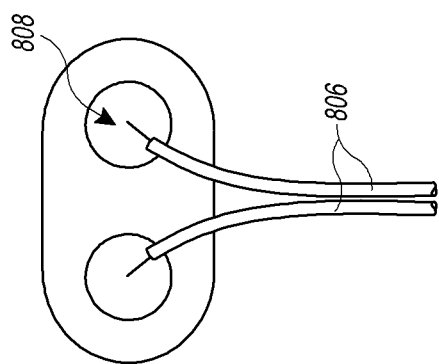
FIG. 17A
FIG. 17C
FIG. 17B

SYSTEMS AND METHODS FOR REVASCULARIZATION ASSESSMENT

CROSS-REFERENCE TO RELATED APPLICATIONS

This application is a continuation of U.S. Ser. No. 16/400,668, filed May 1, 2019, which is a continuation of U.S. Ser. No. 15/892,300, filed Feb. 8, 2018, now abandoned, which is a continuation of U.S. Ser. No. 15/377,864, filed Dec. 13, 2016, now abandoned, which is a continuation of U.S. Ser. No. 14/460,231, filed Aug. 14, 2014, now abandoned, which claims the benefit of priority from U.S. Provisional No. 61/865,977, filed Aug. 14, 2013, and U.S. Provisional No. 61/888,790, filed Oct. 9, 2013, all of which are incorporated by reference in their entireties. This application is also related to U.S. Ser. No. 13/967,298, filed Aug. 14, 2013, which is also incorporated by reference in its entirety.

BACKGROUND

Field

This disclosure relates to the measurement of blood flow in tissue, in particular measurement of blood flow in the foot or other extremities.

Description of the Related Art

The rapidly aging population in the developed world has led to an increasing prevalence of aging-associated degenerative diseases such as peripheral arterial disease and Type 2 diabetes. The manifestations of these include tissue ischemia, chronic wounds and diabetic foot ulcers, where lack of appropriate treatment may lead to infection, gangrene and, in the case of foot ischemia, partial or complete amputation of one or both feet.

Peripheral arterial disease (PAD) is a progressive disease in which narrowed or obstructed arteries reduce blood flow to the limbs. PAD can result from atherosclerosis, inflammatory processes leading to stenosis, an embolism, or thrombus formation, and is associated with smoking, diabetes, dyslipidemia, and hypertension. PAD can if untreated result in critical limb ischemia (CLI), in which blood flow to the limb (usually the legs and feet) is compromised to such an extent that tissue damage ensues with consequent ulceration, gangrene or loss of the limb. Patients with PAD are also at a disproportionately high risk of other cardiovascular diseases like myocardial infarction and stroke and of death as a result of these conditions. With the incidence of diabetes increasing worldwide, treatment of CLI and prevention of disability and of limb loss from it has become a significant health priority.

Peripheral vascular intervention procedures using endovascular (minimally invasive) intervention, open surgery or a combination of the two are currently the only methods available to restore perfusion to the limbs in patients with PAD. Medical management can help only to delay the progression of the disease, if at all. However, clinicians currently lack the intraoperative tools to properly assess perfusion in the affected tissue, usually in the feet, in real-time to reliably guide the conduct of the interventional procedure. Existing technologies that measure blood perfusion include skin perfusion pressure (SPP), duplex ultrasound (DUX), and transcutaneous oxygen monitoring (TCOM). Each of these techniques suffers from one or more disadvantages. SPP only provides perfusion data at the skin dermis level, requires the skin temperature to be normalized to 44° C., is affected by skin pigmentation and is unreliable with patients with edema. SPP also requires the use of a pressure cuff, which further limits its utility as a real-time perfusion assessment tool during peripheral vascular interventions. DUX does not assess tissue perfusion but instead measures blood flow in large vessels (>1.5 mm). TCOM requires the patient to be placed on hyperbaric oxygen, making it incompatible with the cath lab/operating room. Furthermore, TCOM does not provide real time revascularization data as it takes about 4 to 6 weeks for the measurements to equilibrate.

Accordingly, there is a need for noninvasive, real-time measurement of blood perfusion in a range of blood vessel sizes and in the tissue supplied by these vessels. In particular, there is a need for noninvasive, real-time measurement of blood perfusion in the foot that can be reliably performed as the interventional procedure proceeds and be used to inform the decision making during the procedure.

Ischemia is a condition where a restriction of blood supply to tissues leads to a shortage in oxygen and glucose, resulting in irreversible damage to tissues. If discovered too late, reperfusion of blood by various treatment options, thrombolytic or surgical, will only further increase the damage to the tissue as opposed to rescuing the tissue. For example, one of the most common sites of ischemia is the foot. In this case, early detection and diagnosis of an ischemic foot at risk is imperative, before the damage becomes irreversible. Currently, the most common way to diagnose an ischemic foot is ABI (Ankle Brachial Index) which compares the blood pressure in the arm with that at the ankle. An ABI measurement less than 0.9, in some cases, is indicative of an ischemic foot. However, ABI measurements are highly dependent on operator protocol, i.e. different values can be obtained when measurements are obtained with the subject in a seated or supine position, or when the operator uses a different measurement protocol/equipment. ABI also produces falsely elevated measurements in calcified vessels of patients who have diabetes mellitus, are receiving hemodialysis, or if there is an extensive distal arterial lesion below the ankle (Yamada et al, J Vasc Surg 2008; 47: 318-23).

A chronic wound is a non-healing wound that shows little or no improvement after four weeks or does not heal in eight weeks. In practice, patients may present with chronic wounds that remain open for over a year. Around the world, there are 37 million people who suffer from chronic wounds, mostly on the lower limbs. In the US alone, chronic wounds have affected 6.5 million patients and accounted for $1.4 billion in spending in 2010. Since chronic wounds are associated with the diseases of aging, such as diabetes and obesity, the healthcare need for chronic wound management is rising together with the rise in aged populations in the developed world. The early diagnosis of a chronic ischemic wound on lower limbs is particularly important, as it has a major impact in determining whether conservative wound management (e.g., bandages and moist dressings) would be sufficient, or whether more aggressive therapies are required to forestall further wound deterioration that may culminate in amputation.

Conservative therapy for wounds (e.g., bandages, moist dressings) can suffice to facilitate wound healing if the blood perfusion around the wound tissue is not compromised beyond the minimal threshold for passive healing to occur. In cases where the perfusion is compromised, however, the inappropriate use of conservative wound therapy causes a time lag between the first presentment of a wound in a clinical setting to an effective therapy commensurate with the seriousness of the wound condition.

The single most important determinant of tissue viability in a wound is its blood supply. The ability to assess the blood perfusion around the wound bed allows clinical decisions to be made regarding either (a) continuation of conservative therapy if tissue is viable or, (b) if blood perfusion is too severely compromised for successful conservative therapy, to progress early to more advanced wound care products like chemical debriding agents, or advanced wound therapies such as topical negative pressure, hyperbaric oxygen therapy ("HBOT"), etc. In appropriate cases, the patient can be directed to revascularization by peripheral interventional procedures. Hence, a blood perfusion monitor that can facilitate the early streaming of patients into conservative versus aggressive wound therapies is highly desirable.

HBOT involves the administering of oxygen at levels 2-2.5 times sea level in a hyperbaric chamber. A patient may be prescribed up to 40 sessions of HBOT, with typically 3-4 sessions per week, in order to maximize the delivery of oxygen to chronic wound tissue. Such therapy is expensive and is not without risk; its side effects include ear and sinus barotrauma, paranasal sinuses and oxygen toxicity of the central nervous system. (Aviat Space Environ Med. 2000; 71(2):119-24.) Moreover, a retrospective study of 1144 patients (Wound Rep Reg 2002; 10:198-207) indicated that 24.4% of chronic wound patients received no benefit from it. Therefore, a diagnostic device to better predict the success of HBOT in chronic wound treatment will help to avoid unnecessary and unhelpful therapy, and obtain significant cost savings in the healthcare system.

In foot ischemia cases where amputation is required, there is a need for a new diagnostic tool that can better guide decisions regarding the amputation level, by predicting the potential success of amputation wound healing. Amputation is typically performed on patients with severe limb ischemia who cannot be treated with reconstructive vascular surgery, patients with diabetic foot ulcers or venous ulcerations. Approximately 85-90% of lower limb amputations in the developed world are caused by peripheral vascular disease and poor wound healing accounts for 70% of the complication cases that arise from amputation. Due to the lack of optimal tools to predict amputation healing, physicians have to make subjective judgments on the best site for amputation, and since the bias is to maximize limb preservation, it is not uncommon for a patient to require a subsequent amputation higher up the leg when the first amputation wound is unable to heal. The healing rate of below-knee amputation ranges between 30 and 92%, with a re-amputation rate of up to 30%. Thus, an accurate tool for predicting successful amputation healing is needed to help doctors more accurately determine the site of amputation that will result in maximal limb preservation while avoiding the trauma and cost of a revision amputation.

Generally in surgical procedures, particularly in plastic and reconstructive surgery, tissue flaps are used to cover wound defects. These may be either pedicled flaps (i.e. have a vascular pedicle of their own that supplies blood to the flap) or free-flaps that need microvascular connections with the recipient site to ensure adequate blood supply. Both types of flaps are crucially dependent on the blood perfusion within them for the flaps to survive. Flap perfusion needs close monitoring especially in the first few hours to days after the reconstruction procedure and early detection of loss of perfusion will help to direct the patient for further surgical procedures as needed to ensure continued flap viability. It will thus be useful if a diagnostic tool can potentially be used to monitor flap blood perfusion continuously in the post-operative period and prevent flap loss due to delayed detection of flap ischemia.

Currently, diagnostic devices on the market for wound care include duplex ultrasound (for example, as described in EP0814700 A1), transcutaneous oxygen monitoring (TCOM or $TcPO_2$) (for example, as described in WO1980002795 A1), and skin perfusion pressure (SPP) (for example, as described in CA2238512 C), each of which suffer severe disadvantages that limits their effectiveness in administering the right therapy to chronic wound patients. Duplex ultrasound only measures blood flow in large vessels (>1.5 mm). TCOM measurements are not optimally correlated with the status of the wound, (Wounds 2009; 21(11):310-316). This is especially so as TCOM measurements are influenced by many factors including local edema, anatomical localization, thickness of the epidermal stratum corneum, and leg dependency (Figoni et al, J. Rehab Research Development 2006; 43 (7) 891-904). In addition, test results are heavily affected by moisture and temperature levels (Podiatry Today 2012; 25(7) 84-92). Lo et al. (Wounds 2009:21(11) 310-316) report that skin perfusion pressure (measured by laser Doppler) appears to be a more accurate predictor of wound healing versus $TcPO_2$; however SPP is only able to provide data at limited depth and requires skin temperature to be normalized to 44° C., is sensitive to skin pigmentation and unreliable with edema.

Most recently, the use of diffuse speckle contrast analysis (DSCA) has been developed to measure real-time blood perfusion in tissue depths of up to two centimeters (2 cm), in absolute BFI ("blood flow index") units (as described in more detail in U.S. Provisional App. Nos. 61/755,700, filed Jan. 23, 2013, and 61/830,256, filed Jun. 3, 2013, each of which are hereby incorporated by reference in their entirety). The present disclosure centers on the use of DSCA to generate additional information, such as low frequency oscillation data that forms the basis of a calibrated index that can guide clinical decisions in treating ischemia.

SUMMARY

Disclosed herein is a system for assessment of peripheral blood flow during peripheral vascular intervention, the system including: a support structure configured to be positioned onto a patient's foot; a diffuse optical flow (DOF) sensor carried by the support structure; an analyzer configured to analyze data from the DOF sensor to determine absolute and/or relative blood flow at a location near the DOF sensor when the support structure is positioned onto a patient's foot; and a feedback device configured to provide a signal indicative of the absolute and/or relative blood flow determined by the analyzer.

In some embodiments, the support structure can include a retention ring and an adhesive material, or simply an adhesive material. In some embodiments, the support structure can include a strap having the DOF sensor attached thereto. In some embodiments, the DOF sensors can be arranged such that when the support structure is positioned onto the patient's foot, at least two of the DOF sensors are over different topographical locations in the foot including different pedal angiosomes. In some embodiments, the DOF sensors can be arranged such that when the support structure is positioned onto the patient's foot, at least five of the DOF sensors are over different topographical locations in the foot including different pedal angiosomes. In some embodiments, the analyzer can include a software autocorrelator. In some embodiments, the analyzer can include a hardware autocorrelator. In some embodiments, the signal indicative of the absolute and/or relative blood flow can be visual, audible, or tactile. In some embodiments, the system can be configured to provide the signal indicative of the absolute and/or relative blood flow in substantially real-time. In some embodiments, the system can be configured to provide the signal indicative of the absolute and/or relative blood flow within 1 second from measurement.

Also disclosed herein is a method for real-time assessment of peripheral blood flow during peripheral vascular intervention procedures, the method including: disposing at least one diffuse optical flow (DOF) sensor adjacent to a location on a foot of a patient; obtaining measurements of intensity fluctuation from the DOF sensor; analyzing the obtained measurements to determine an absolute and/or relative blood flow rate at the location; and signaling the determined absolute and/or relative blood flow rate to an operator.

In some embodiments, disposing the at least one DOF sensor can include placing a support structure onto the foot of the patient, the DOF sensor being carried by the support structure. In some embodiments, the method can further comprise disposing a plurality of DOF sensors adjacent to a respective plurality of locations on the foot of the patient. In some embodiments, the plurality of locations can include at least two, three, four, five, or more locations corresponding to different topographical locations in the foot including different pedal angiosomes. In some embodiments, plurality of locations can include at least five locations corresponding to five different topographical locations in the foot including different pedal angiosomes. In some embodiments, signaling can include providing visual, audible, or tactile indicia of absolute and/or relative blood flow. In some embodiments, signaling the determined absolute and/or relative blood flow rate to an operator can be performed in less than 1 second from measurement.

Further disclosed is a method for assessment of peripheral blood flow during peripheral vascular intervention procedures, the method including: disposing a plurality of diffuse optical flow (DOF) sensors adjacent to a respective plurality of locations on an extremity of a patient, wherein at least two of the locations correspond to different topographical locations in the foot including different pedal angiosomes; determining an absolute and/or relative blood flow rates at each of the plurality of locations in the extremity of the patient; and signaling the determined absolute and/or relative blood flow rates to an operator.

In some embodiments, the extremity can be a foot. In some embodiments, the extremity can be a hand. In some embodiments, the signaling can be performed in substantially real-time. In some embodiments, the determined absolute and/or relative blood flow rates can be utilized to assess the efficacy of an interventional procedure.

Also disclosed herein is a patient interface, for supporting a plurality of diffuse optical flow (DOF) sensors in optical communication with a patient's foot, comprising: a support, configured to be mountable on and carried by the foot; at least three sensors carried by the support, each sensor corresponding to a separate topographical location in the foot including an angiosome selected from the group consisting of: the angiosome of the medial plantar artery; the angiosome of the lateral plantar artery; the angiosome of the calcaneal branch of the posterior tibial artery; the angiosome of the calcaneal branch of the peroneal artery; and the angiosome of the dorsalis pedis artery.

In some embodiments, the patient interface can include at least four sensors carried by the support, each sensor corresponding to a separate topographical location in the foot including a pedal angiosome. In some embodiments, the support can comprise a retention ring and adhesive material. In some embodiments, the support can comprise an optical source fiber and an optical detector fiber. In some embodiments, the optical source fiber and the optical detector fiber can further comprise at least one coupling for releasably coupling the sensor to an analyzer. In some embodiments, the patient interface can comprise a cable, which includes a plurality of pairs of source fibers and detector fibers, each pair connected to a separate sensor. In some embodiments, each sensor can be releasably carried by the support.

Also disclosed herein is a system for assessment of peripheral blood perfusion, the system including: a support structure configured to be positioned onto a patient's foot; a diffuse optical sensor carried by the support structure; an analyzer configured to analyze data from the diffuse optical sensor to characterize the composition or flow of blood at a location near the diffuse optical sensor when the support structure is positioned onto a patient's foot; and a feedback device configured to provide a signal indicative of composition or flow of blood determined by the analyzer.

Further disclosed herein is a method for real-time assessment of peripheral blood, the method including: disposing at least one diffuse optical sensor adjacent to a location on a foot of a patient; obtaining measurements of diffused light; analyzing the obtained measurements to characterize the composition and/or flow rate of blood at the location; and signaling the determined composition and/or flow rate to an operator. In some embodiments, sensors disclosed herein do not take pressure measurements, e.g., blood pressure measurements.

Also disclosed is a method for assessment of peripheral blood flow during peripheral vascular intervention procedures, the method including: disposing a plurality of diffuse optical sensors adjacent to a respective plurality of locations on an extremity of a patient, wherein at least two of the locations correspond to different topographical locations in the foot including different pedal angiosomes; characterizing the composition and/or blood flow rates at each of the plurality of locations in the extremity of the patient; and signaling the composition and/or blood flow rates to an operator.

Further disclosed herein is a patient interface, for supporting a plurality of diffuse optical sensors in optical communication with a patient's foot, comprising: a support, configured to be mountable on and carried by the foot; at least three sensors carried by the support, each sensor corresponding to a separate topographical location in the foot including angiosome selected from the group consisting of: the angiosome of the medial plantar artery; the angiosome of the lateral plantar artery; the angiosome of the calcaneal branch of the posterior tibial artery; the angiosome of the calcaneal branch of the peroneal artery; and the angiosome of the dorsalis pedis artery.

Disclosed herein is a system for using Low Frequency Oscillation Index ("LFI") in blood flow measurements as a diagnostic index for ischemic tissue management. In some embodiments, blood perfusion can be measured as a function of time to provide time series data. Measurement of blood perfusion can be accomplished by a number of different techniques, including, without limitation, diffuse correlation spectroscopy (DCS), diffuse speckle contrast analysis (DSCA), diffuse optical tomography, near-infrared spectroscopy, or Doppler flowmetry. In some embodiments, blood perfusion can be measured by non-optical techniques, for example via electrical or magnetic blood flow measurement techniques. In some embodiments, blood perfusion can be measured at a depth of at least about 1 mm below the skin. In some embodiments, blood perfusion can be measured at a depth of at least about 3 mm below the skin. In some embodiments, blood perfusion can be measured at a depth of at least about 5 mm below the skin. The tissue of interest can generally be in the lower limbs especially if the system is used to assess peripheral vascular disease. In other applications, the tissue of interest may be surgical tissue flaps used in plastic and reconstructive surgery.

The obtained time series data may then be analyzed to obtain relevant parameters for use in clinical applications. For example, the time series data may be transformed into a power spectrum. In some embodiments, a Fourier transform may be used to transform the time series data into a power spectrum. In some embodiments, a Fast Fourier Transform may be used. In other embodiments, a wavelet transform can be used to obtain the power spectrum.

Once the power spectrum is obtained, one or more parameters may be calculated and used to guide clinical judgment. In some embodiments, parameters can be calculated from the power spectrum over a specific frequency range. In some embodiments, the frequency range can be between about 0.001 Hz to about 1000 Hz, between about 0.001 Hz and about 0.1 Hz, between about 0.045 Hz and about 0.01 Hz, or between 0.001 Hz to about 0.045 Hz. The calculated parameter can be the area under the curve of the power spectrum within the specified frequency range. In some embodiments, the calculated parameter can be the local maximum power of the power spectrum within the specified frequency range.

In other embodiments, the calculated parameter may be the Pearson correlation coefficient calculated between the time-series data of blood flow obtained from at least two locations on the patient. In some instances, these two locations may be the calcaneal and the arm respectively. In other instances, the locations may be the medial plantar and the arm.

In still another embodiment, the calculated parameter may be the Pearson correlation coefficient calculated between the frequency domain spectrum obtained from at least two locations on the patient In some embodiments, the calculated parameter may be the relative power.

In some embodiments, the calculated parameters may be processed by a State Vector Machine (SVM).

The calculated parameter may then be used for any one of a number of clinical evaluations. For example, the calculated parameter can be used to distinguish between healthy and ischemic limbs, such as healthy and ischemic feet. The parameter may be used in some embodiments to identify patients who may have endothelial or other vascular dysfunction that may impact wound healing. In some embodiments, the calculated parameter can be used to screen claudicant patients for interventional therapy. In some embodiments, the calculated parameter can be used to predict the likelihood of success for conservative wound therapy. In some embodiments, the calculated parameter can be used to determine the need for advanced wound therapy or interventional procedures, such as balloon angioplasty or vascular surgery. The calculated parameter may also be used in some embodiments to predict the likelihood of success of an amputation site healing. In some embodiments, the calculated parameter can be used to predict the likelihood of success of a hyperbaric oxygen therapy for chronic wound healing. In some embodiments, the calculated parameter can be used to predict the likelihood of success of surgical flaps.

In some embodiments, the calculated parameter can be used to predict the uptake of drugs.

The measurement can be obtained locally, such as at the target site such as on the patient's foot. In some embodiments, mathematically transforming the time-series data and/or calculating a parameter can also be conducted locally. In some embodiments, the mathematical transform and/or calculating a parameter can be conducted remotely from the measurement site. For example, the measurement may be obtained locally, and the obtained time-series data may be transmitted to a remote location for further processing. In some embodiments, this can enable remote monitoring of a patient. Time series data can be obtained by a probe worn by the patient, while the monitoring physician or other individual can be located remotely, and can receive the obtained time series data for further processing and evaluation. In various embodiments, the processing (e.g., mathematical transform and calculation of parameters) can be conducted in software, in hardware, or some combination thereof. In some embodiments, the processing can be conducted on a local device such as a general purpose computer, while in other embodiments the processing can be conducted via a distributed network.

Also disclosed herein are systems for discriminating between at least a first population and a second population. The systems can include one or more of a processor configured to receive blood perfusion measurements as a function of time to obtain time series data; mathematically transform the time series data into a power spectrum; calculate at least one parameter of the power spectrum within a specific frequency range; and/or use the at least one calculated parameter as a discriminator for the first population and the second population. The first population and the second population can comprise two patient populations, such as, for example, a healthy control group and an ischemic population. The system can also include at least one optical and/or non-optical sensor configured to measure blood perfusion as a function of time. The optical sensor can include a diffuse optical flow sensor. The processor can be configured to mathematically transform the time series data into a power spectrum using a Fourier transform, a fast Fourier Transform, or a wavelet transform. The specific frequency range can be, for example, between about 0.001 Hz and about 1000 Hz, between about 0.001 Hz and about 0.1 Hz, between about 0.045 Hz and about 0.1 Hz, or between about 0.001 Hz and 0.045 Hz. The parameter could be, for example, an area under the curve of the power spectrum within the specific frequency range, or the local maximum power of the power spectrum within the frequency range of interest.

Also disclosed herein is a method for discriminating between at least a first population and a second population. The method can include the steps of: measuring blood perfusion as a function of time to obtain time series data; calculating statistical parameters from the time series data; and using at least one of the statistical parameters as a discriminator for the first population and the second population.

In some embodiments, various statistical parameters can be determined from data obtained relevant to blood flow of one, two, or more patients or patient populations, including one or more of a standard deviation, a mean, a median, a mode, a correlation coefficient, a linear regression, a Z score, a p value, a Chi-Squared test, and a Fisher's exact test.

Blood flow can be measured using optical (e.g., diffuse optical) and/or non-optical flow sensors. Systems are also disclosed for discriminating between at least a first population and a second population. The systems can include a processor module configured to receive blood perfusion measurements as a function of time to obtain time series data; calculate at least one statistical parameter from the time series data; frequency range; and use the at least one calculated parameter as a discriminator for the first population and the second population. The sensors can be configured to send blood perfusion measurements through a wired or wireless connection to the processor.

Also disclosed herein are computer-implemented methods for discriminating between at least a first population and a second population. The methods can include any number of the following steps: sensing blood flow rate at a first anatomical location; sending data relating to the blood flow rate to a module; sensing blood perfusion at a second anatomical location; determining a second blood flow index at the second anatomical location; calculating the ratio of the first blood flow index to the second blood flow index; and determining whether the ratio corresponds to a characteristic of the first population or the second population by comparing the ratio to a predetermined threshold value. The method can also include the step of providing a signal to an operator related to the ratio. The first anatomical location can be the foot, and the second anatomical location can be a location that is not directly perfused by an artery of the foot. The second anatomical location can be selected from the group consisting of: the thumb, the earlobe, the upper arm, and the thenar eminence. The first population can be, for example, an ischemic population, and the second population can be, for example, a non-ischemic population.

Also disclosed herein is a system for discriminating between at least a first population and a second population. The system can include a processor configured to perform one or more of the following steps: receive blood perfusion data from a first sensor at a first anatomical location; determine a first blood flow index at the first anatomical location; receive blood perfusion data from a second sensor at a second anatomical location; determine a second blood flow index at the second anatomical location; calculate the ratio of the first blood flow index to the second blood flow index; and determine whether the ratio corresponds to a characteristic of the first population or the second population by comparing the ratio to a predetermined threshold value. The system can also include the first sensor configured to obtain blood perfusion data from a first anatomic location, and the second sensor configured to obtain blood perfusion data from the second anatomic location.

Also disclosed herein is a computer-implemented method for discriminating between at least a first population and a second population. The method can include any number of the following steps: sensing a blood flow rate at a first anatomical location; sending data relating to the blood flow rate to a module configured to analyze the data relating to the blood flow rate; calculating a numerical value derived from the data relating to the blood flow rate; determining whether the calculated value corresponds to a characteristic of the first population or the second population by comparing the ratio to a predetermined threshold value; and providing a signal to an operator relating to the calculated value. The first anatomical location can be the foot. Calculating the numerical value can comprise calculating a statistical parameter from the data relating to the blood flow rate, or characterizing the blood flow rate as a function of a specified time interval. The statistical parameter can be, for example, a standard deviation. The method can also include calculating the numerical value comprises calculating a power spectrum parameter from the data relating to the blood flow rate, or calculating a ratio derived from the data relating to the blood flow rate.

Also disclosed herein is a system for discriminating between at least a first population and a second population. The system can include any number of the following: a module configured to receive blood flow rate data from a first sensor at a first anatomical location; calculate a numerical value derived from the data relating to the blood flow rate; determine whether the calculated value corresponds to a characteristic of the first population or the second population by comparing the ratio to a predetermined threshold value; and provide a signal to an operator relating to the calculated value.

BRIEF DESCRIPTION OF THE DRAWINGS

FIG. 8A shows the raw BFI data (raw time series BFI data) measured at the medial plantar section of the foot of two individuals, one healthy versus one with indications of limb ischemia, while

FIGS. 9A and 9B illustrate boxplots of low frequency oscillation index (LFI) from 26 healthy and 26 ischemic patients, assessed in two different methods: maximum-based ($LFI_M$) in FIG. 9A, and area-based ($LFI_A$) in FIG. 9B.

FIG. 11 illustrates a ROC curve for a 5-dimensional SVM utilizing patient BFI input parameters.

Figure 13B:
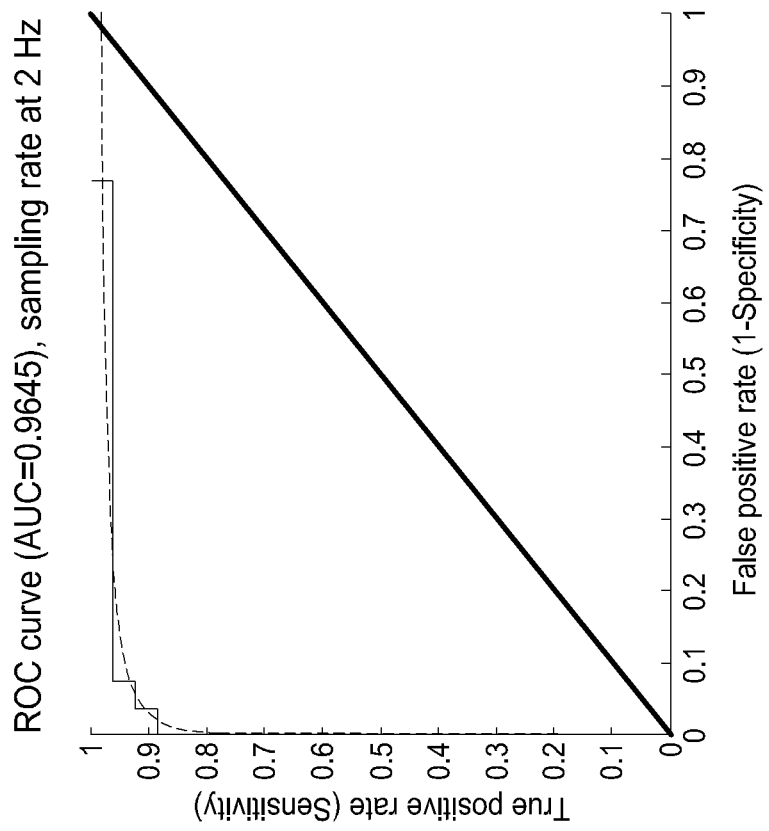
Figure 13A:
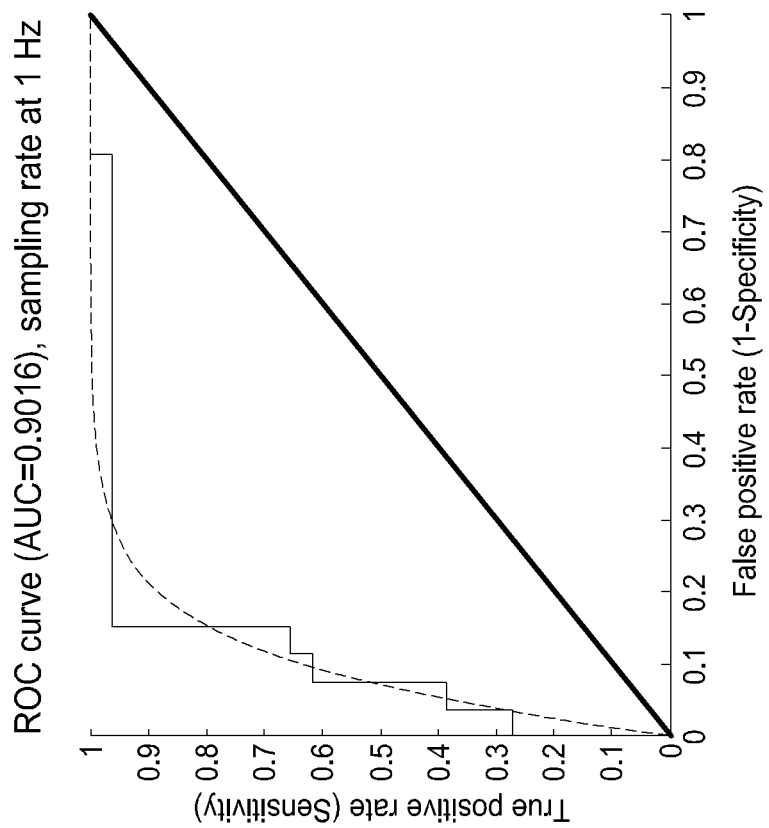

The standard deviation of 5 minutes of Medial Plantar BFI data sampled at 1 Hz and 2 Hz was calculated, and the resulting ROC curves are shown in FIGS. 13A and 13B.

FIG. 13A illustrates the ROC of Standard Deviation of BFI@ 1 Hz; FIG. 13B illustrates the ROC of Standard Deviation of BFI@ 2 Hz.

Figure 14A:
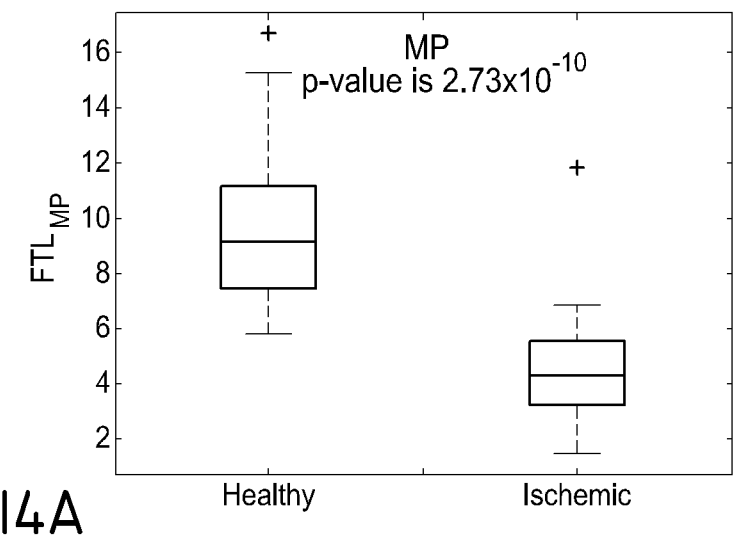
Figure 14B:
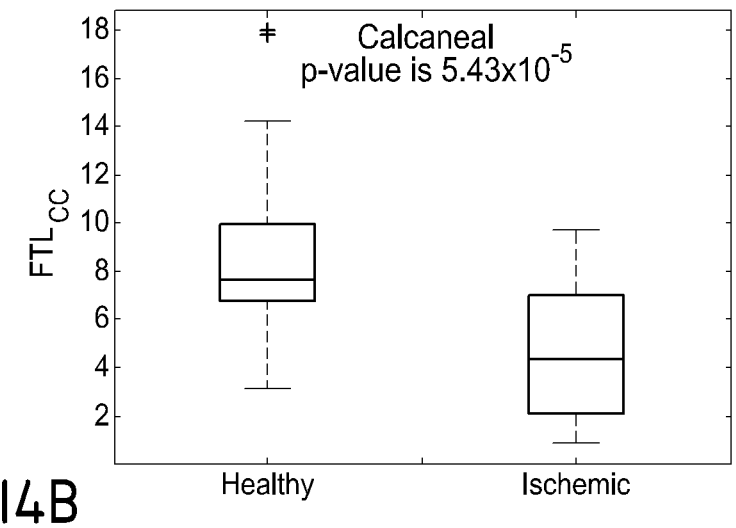
Figure 14C:
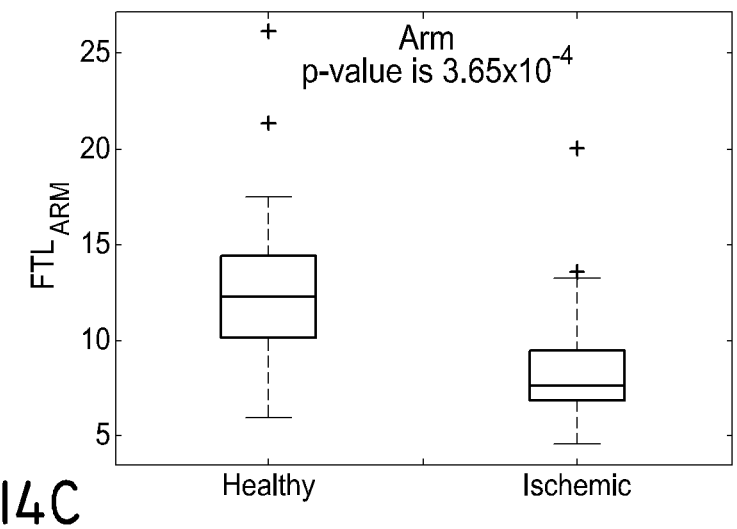
Figure 14D:
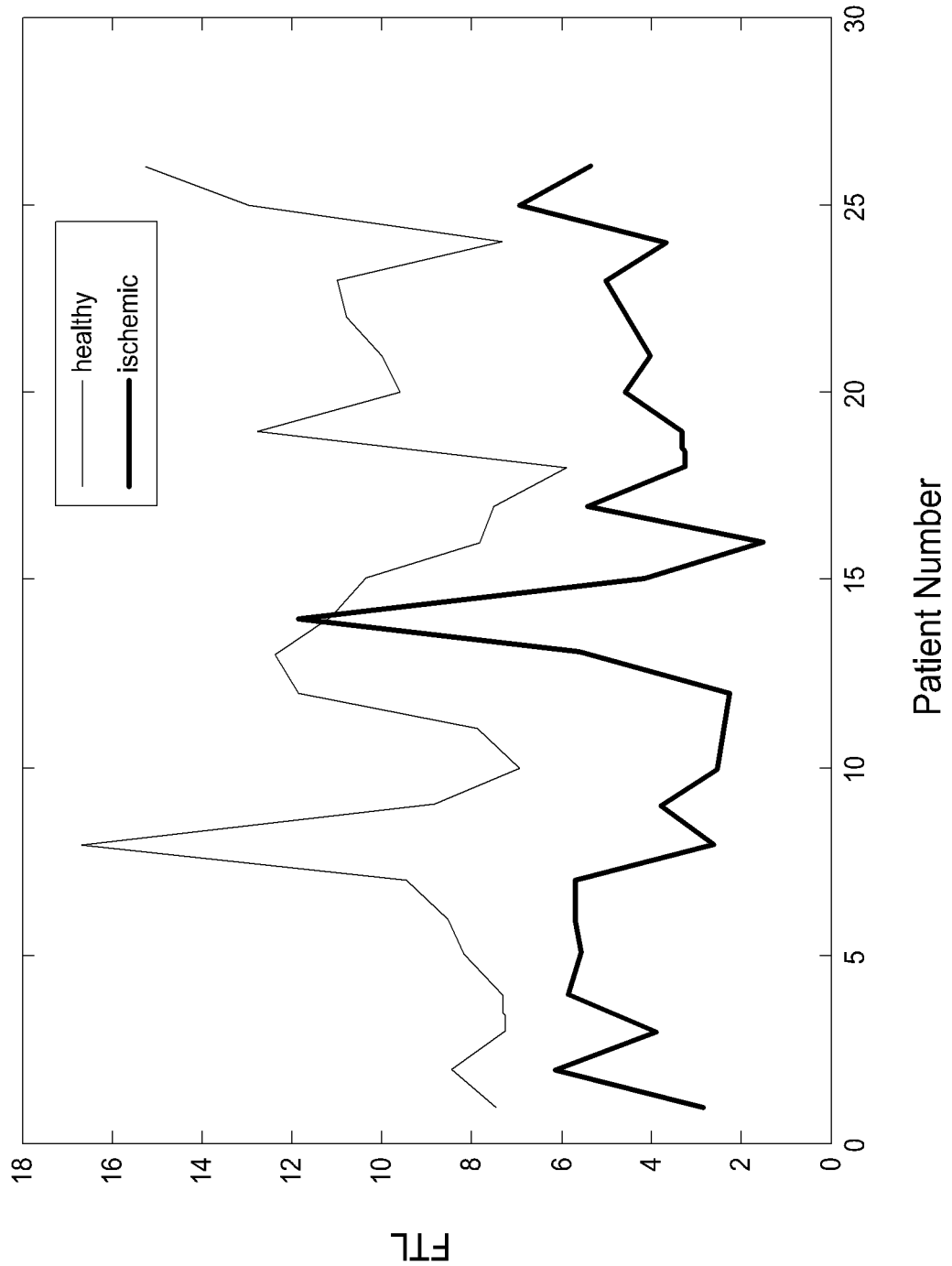

The Standard Deviation of BFI from calcaneal and arm also shows significant difference between healthy and ischemic patients, but not strongly as with the medial plantar. The p-values of three positions are compared in FIGS. 14A-14C, which are box plots of FTLs in the medial plantar, calcaneal, and arm regions, respectively. FIG. 14D illustrates FTL values for a number of patients including healthy and ischemic patient populations.

FIG. 15A is a schematic illustration of a side-firing DOF sensor.

FIG. 15B illustrates a cover sock.

FIG. 15C illustrates a cover sock having a plurality of embedded side-firing DOF sensors.

Figure 15D:
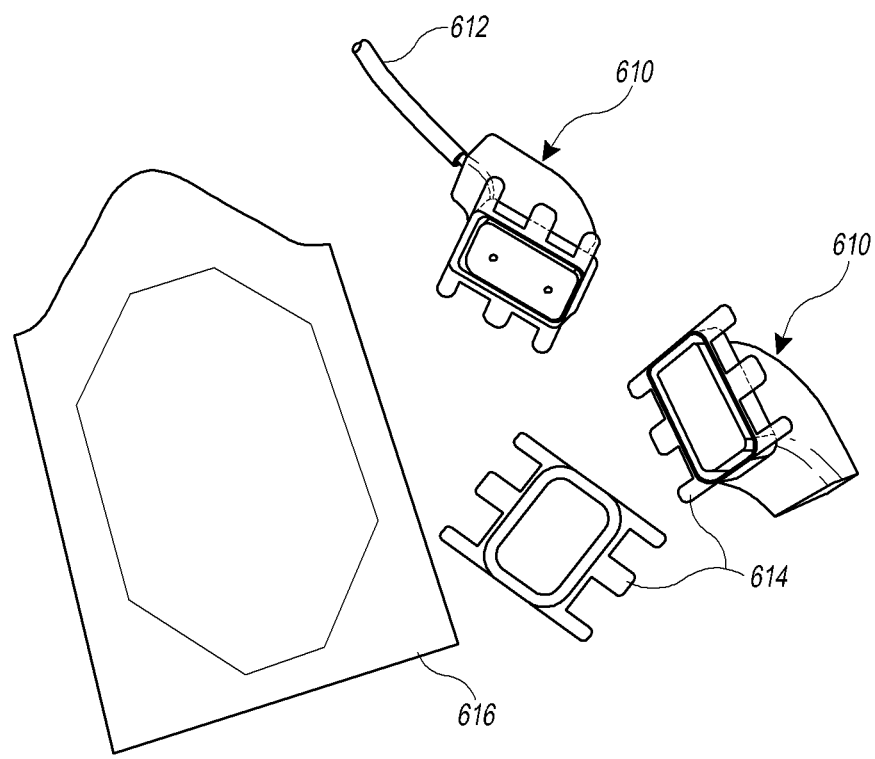

FIG. 15D illustrates another embodiment of a DOF sensor, with a retention ring and adhesive material.

Figure 15E:
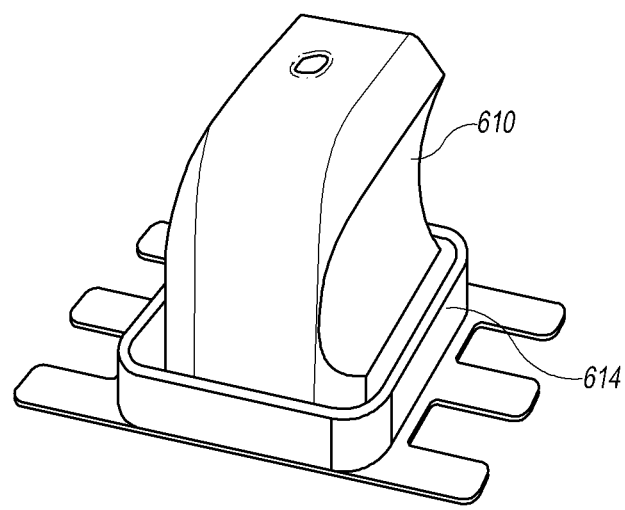

FIG. 15E illustrates a detail view of the DOF sensor head shown in FIG. 15D.

Figure 16:
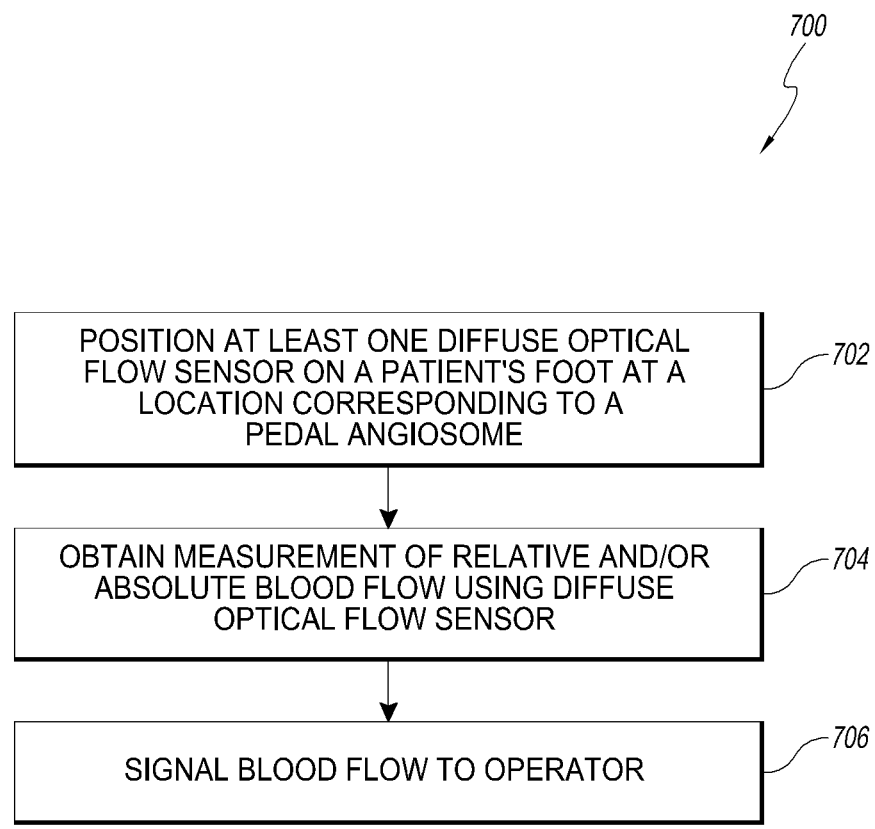

FIG. 16 is a flow diagram of a method for analyzing absolute and/or relative blood flow.

FIGS. 17A-17C illustrate an embodiment of a DOF sensor, with a horizontal sensor head.

FIGS. 18A-18D illustrate another embodiment of a DOF sensor with a horizontal sensor head.

Figure 19:
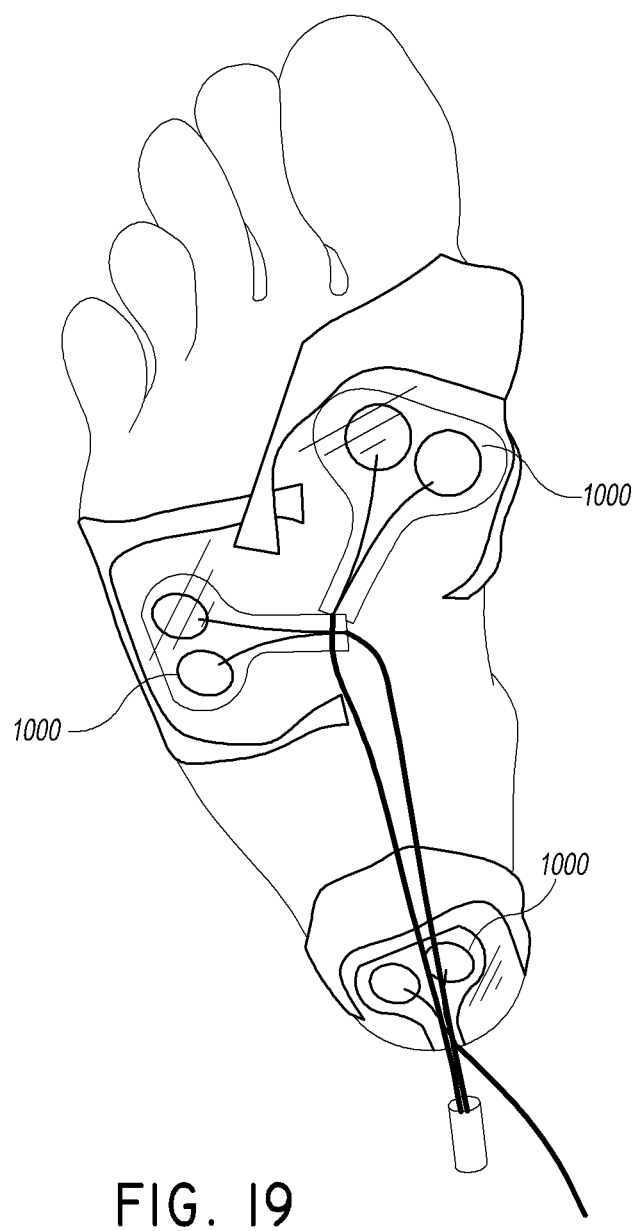

FIG. 19 illustrates a DOF sensor attached to a patient's foot.

Figure 20:

FIG. 20 illustrates a DOF sensor attached to a patient's hand.

DETAILED DESCRIPTION

Diffuse Optical Flow Sensors

A number of techniques exist for characterizing blood flow (which may also be referred to herein as blood perfusion), relying on measuring of diffusion of light. Such techniques include Diffuse Correlation Spectroscopy (DCS) and Diffuse Speckle Contrast Analysis (DSCA). Both DCS and DSCA can be used to measure relative and/or absolute blood flow. Other techniques rely on measuring diffusion of light to detect other characteristics of tissue, such as biochemical composition, concentrations of oxyhemoglobin and deoxyhemoglobin, etc. Such techniques include Diffuse Optical Spectroscopy (DOS), Diffuse Optical Tomography (DOT), and Near-Infrared Spectroscopy (NIRS).

As used herein, "diffuse optical sensor" includes any sensor configured to characterize properties of blood in tissue via measurement of diffuse light. As such, diffuse optical sensors include DCS, DSCA, DOS, DOT, and NIRS sensors. As used herein, the term "diffuse optical flow sensor" includes any sensor configured to characterize blood flow in tissue. As such, diffuse optical flow (DOF) sensors include both DCS and DSCA sensors.

Near-infrared diffuse correlation spectroscopy (DCS) is an emerging technique for continuous noninvasive measurement of blood flow in biological tissues. In the last decade or so, DCS technology has been developed to noninvasively sense the blood flow information in deep tissue vasculature such as brain, muscle, and breast. In contrast to some other blood flow measurement techniques, such as positron emission tomography (PET), single photon emission computed tomography (SPECT), and xenon-enhanced computed tomography (XeCT), DCS uses non-ionizing radiation and requires no contrast agents. It does not interfere with commonly used medical devices such as pacemakers and metal implants. It therefore has potential in cancer therapy monitoring and bedside monitoring in clinical settings.

A DCS system can include a light source such as a laser with a long coherence length, a detector such as a photon-counting avalanche photodiode (APD) or photomultiplier tube (PMT), and an autocorrelator. In various embodiments, the autocorrelator may take the form of hardware or software. As one of the central components of the DCS system, the autocorrelator computes the autocorrelation function of the temporal fluctuation of the light intensity obtained from the detector.

However, DCS can suffer from a long integration time, high cost, and low channel number of simultaneous measurements. One factor contributing to these limitations is dependence on very sensitive photodetector(s) and subsequent autocorrelation calculation. Diffuse Speckle Contrast Analysis (DSCA) is a newer technology that provides an improved flowmetry system enabling cost-effective, real-time measurements using statistical analysis without having to rely on autocorrelation analysis on fast time-series data. This statistical analysis can be implemented either in spatial domain using a multi-pixel image sensor, or in the time domain using slow counter. A multi-pixel image sensor can also be used for time domain analysis such that single or multiple pixels act as an individual detector, which is especially suitable for multi-channel application. In various embodiments, this approach can be used to measure blood flow, whether absolute, relative, or both.

DSCA can be implemented in both spatial and time domains. For spatial DSCA (sDSCA), a raw speckle image is first obtained from the sample surface. The raw speckle images may first be normalized by the smooth intensity background, which can be averaged over a number of speckle images. The speckle contrast, $K_s$ is defined as the ratio of the standard deviation to the mean intensity across many detectors or pixels, $K_s = \sigma_s/<I>$, where subscript s refers to the spatial, as opposed to temporal, variations. The quantity $K_s$ is related to the field autocorrelation function $g_1(\tau)$ as follows:

$$V(T) = [K_s(T)]^2 = \frac{2}{T}\int_0^T (1-\tau/T)[g_1(\tau)]^2 d\tau$$

where V is the intensity variance across the image, and T is the image sensor exposure time. By using the known solution of the correlation diffusion equation in the semi-infinite medium, the formal relationship between the flow rate and $K_s$ can be derived. The relationship between the flow and $1/K_s^2$ turns out to be substantially linear in the range of flow seen in body tissue, with $1/K_s^2$ increasing with increasing flow rate.

Another way to implement this speckle contrast rationale for flowmetry is to use statistical analysis on time series data obtained by integrating over a certain time. This temporal domain analysis is referred to herein as tDSCA. The integrating time for tDSCA can be regarded as analogous to the exposure time of the image sensor in sDSCA. In the case of tDSCA, a detector with moderate sensitivity with an integrating circuit can be used. For example, each pixel on a CCD chip can be used for this purpose as each CCD pixel keeps accumulating photoelectrons for a given exposure time. Therefore, a number of single-mode fibers can be directly positioned on some locations on a single CCD chip, resulting in a multi-channel tDSCA system without losing any time resolution. The number of channels is only limited by the CCD chip size, pixel size, and the area of each fiber tip. In some embodiments, tDSCA can use sensitive detectors such as avalanche photodiode (APD) and/or photomultiplier tube (PMT) with a slow counter such as a counter included in a DAQ card with USB connection, but scaling this embodiment to multichannel instrument is costly and bulky. Time-series data taken either way can be obtained by repeat measurements, for example 25 measurements can be made consecutively, after which the data can be analyzed statistically to determine the flow rate. In a configuration with an exposure time of 1 ms, one flow index would be obtained every 25 ms, resulting in approximately 40 Hz operation.

The statistical analysis of the time-series data can be substantially identical to that described above with respect to sDSCA, except that the statistics (average intensity and standard deviation of intensity) are calculated in the time domain, rather than the spatial domain. As a result, tDSCA may provide lower time resolution than sDSCA. However, the detector area for tDSCA may be significantly smaller than with sDSCA. As with the spatial domain counterpart, tDSCA provides an approach with instrumentation and analysis that are significantly simpler and less computationally intensive than traditional DCS techniques.

Both DCS and DSCA technology can be used to evaluate on a real-time basis the absolute and/or relative blood flow in the foot, thereby providing an important tool for interventional radiologists and vascular surgeons treating ischemia in the foot. With current tools in the operating room, the physician can usually assess via X-ray fluoroscopy whether an intervention such as a balloon angioplasty procedure has succeeded in opening up and achieving patency of a limb artery. However, the clinical experience has been that structural patency as observed with fluoroscopy is not a reliable indicator of successful reperfusion of the topographical region of the foot where the ulcer wound, ischemic tissue (e.g., blackened toes) or other clinical manifestation is located. To augment fluoroscopic data on arterial patency, a plurality of DOF sensors used in either DCS or DSCA systems can be positioned at different topographical regions of the foot to assess absolute and/or relative blood flow in the different regions. For example, the topographical regions may correspond to different pedal angiosomes.

An angiosome is a three-dimensional portion of tissue supplied by an artery source and drained by its accompanying veins. It can include skin, fascia, muscle, or bone. Pedal angiosomes are illustrated in FIG. 1A. Below the knee, there are three main arteries: the anterior tibial artery, the posterior tibial artery, and the peroneal artery. The posterior tibial artery gives at least three separate branches: the calcaneal artery, the medial plantar artery, and lateral plantar artery, which each supply distinct portions of the foot. The anterior tibial artery supplies the anterior ankle and continues as the dorsalis pedis artery, which supplies much of the dorsum of the foot. The calcaneal branch of the peroneal artery supplies the lateral and plantar heel. The anterior perforating branch of the peroneal artery supplies the lateral anterior upper ankle. As a result, the pedal angiosomes include: the angiosome of the medial plantar artery, the angiosome of the lateral plantar artery, the angiosome of the calcaneal branch of the posterior tibial artery, the angiosome of the calcaneal branch of the peroneal artery, the angiosome of the dorsalis pedis artery. There is some debate as to whether there is a separate sixth pedal angiosome corresponding to the anterior perforating branch of the peroneal artery.

Figure 1B:
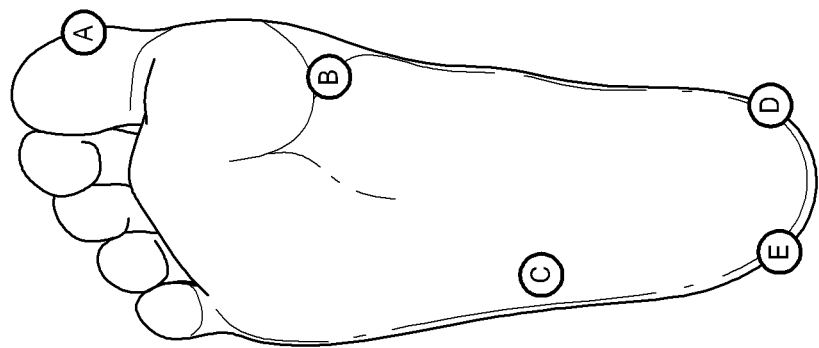
FIG. 1B illustrates five measurement points on the foot, each corresponding to one of the angiosomes shown in FIG. 1A.
Figure 1A:
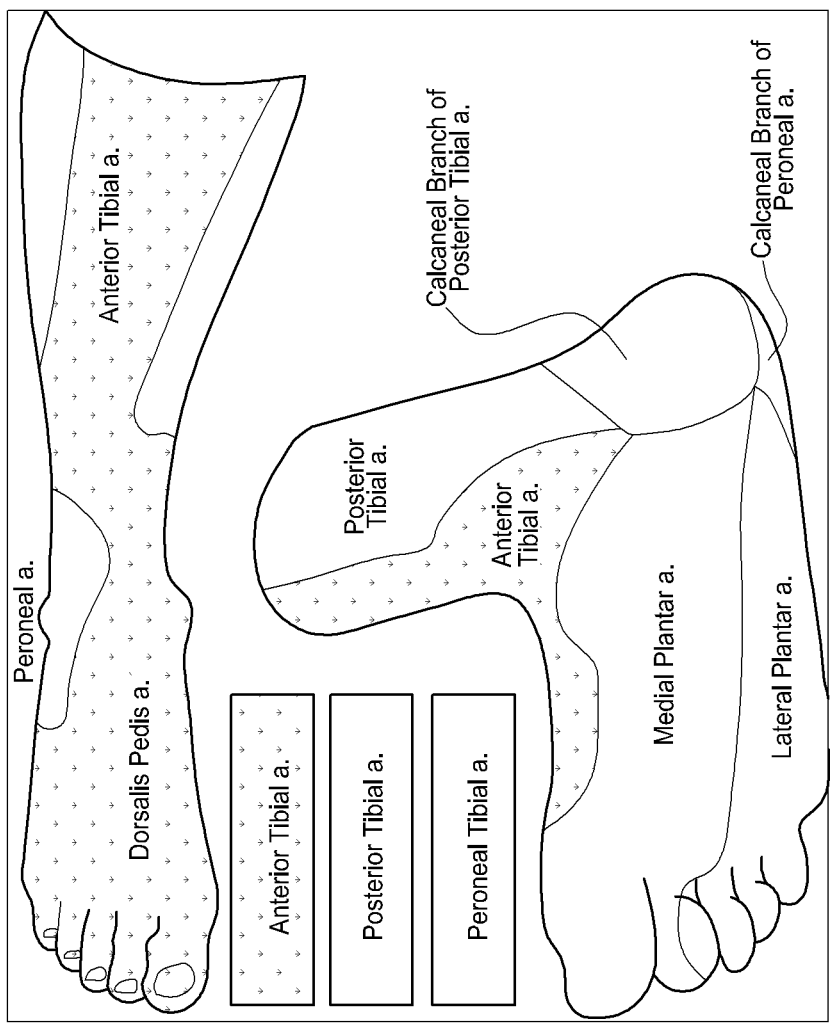
FIG. 1A illustrates the pedal angiosomes.

FIG. 1B illustrates five measurement points on the foot, each corresponding a pedal angiosome identified in FIG. 1A. By detecting blood flow in each of these positions, blood flow from the various arteries can be evaluated independently. For example, measurement of blood flow at point A (see FIG. 1D) is indicative of blood flow from the dorsalis pedis artery, and also the anterior tibial artery. Similarly, measurement of blood flow at point B (see FIG. 1E) corresponds to the medial plantar artery, while point C (see FIG. 1F) corresponds to the lateral plantar artery, point D (see FIG. 1G) corresponds to the calcaneal branch of the posterior tibial artery, and point E (see FIG. 1H) corresponds to the calcaneal branch of the peroneal artery.

Figure 1C:
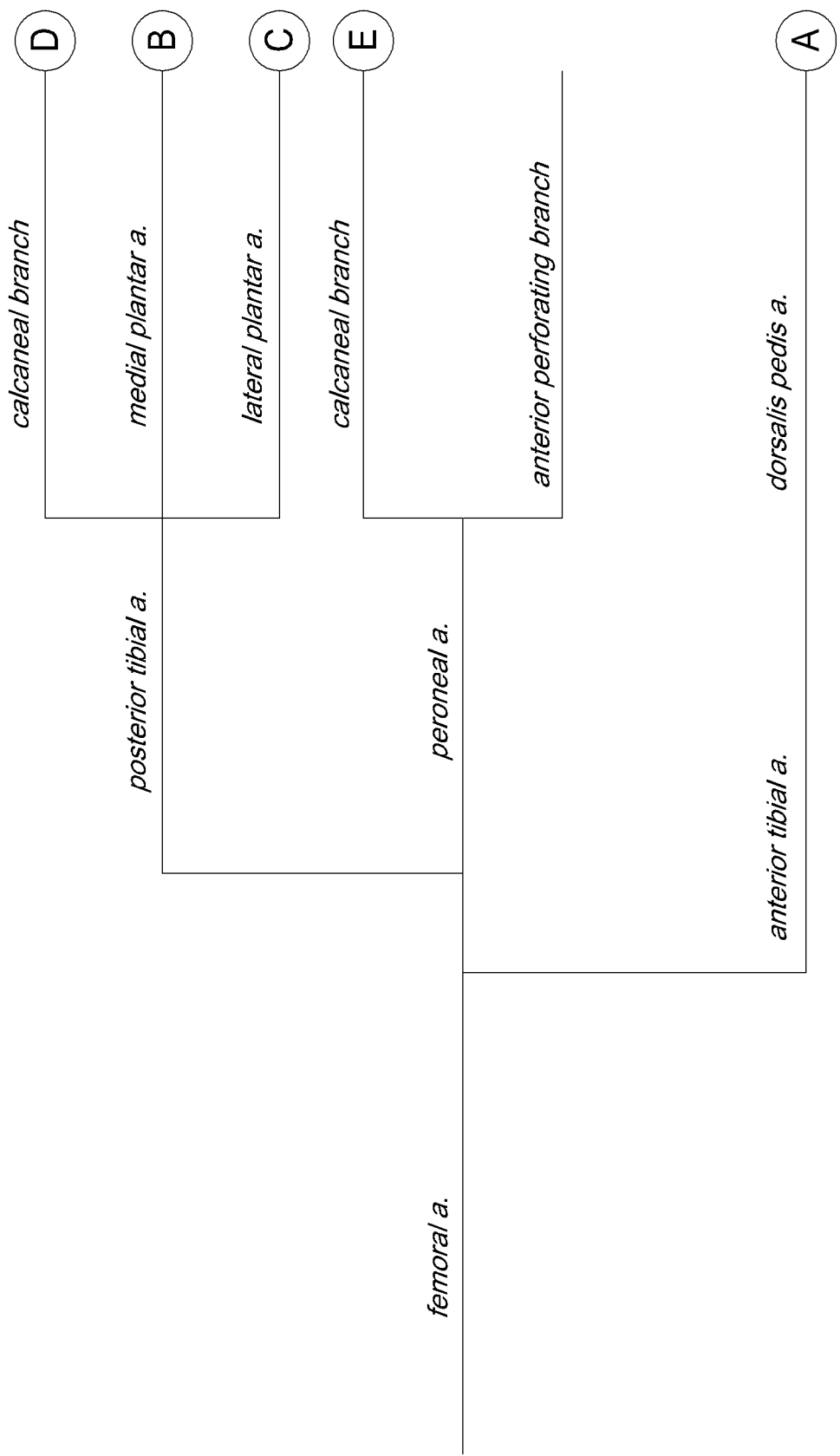
FIG. 1C illustrates the branching of the arteries supplying the pedal angiosomes.
Figure 1F:
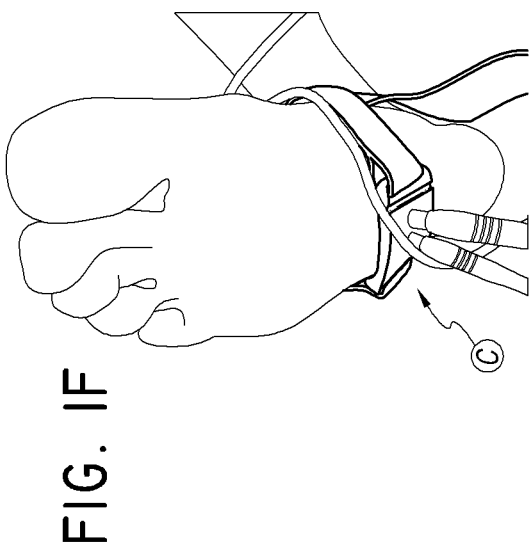
FIGS. 1D-1H illustrate measurement using diffuse optical flow (DOF) sensors at each of the five measurement positions of FIG. 1B.
Figure 1H:
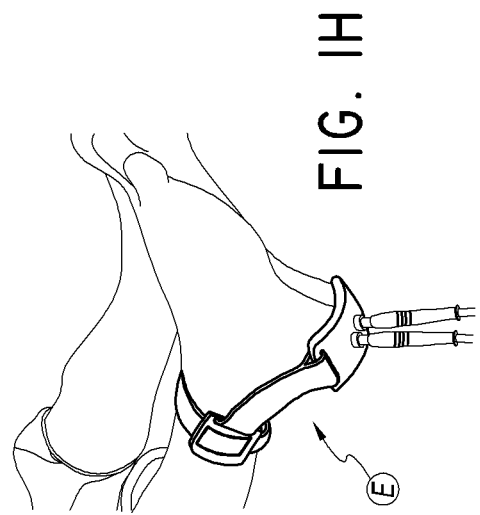
Figure 1E:
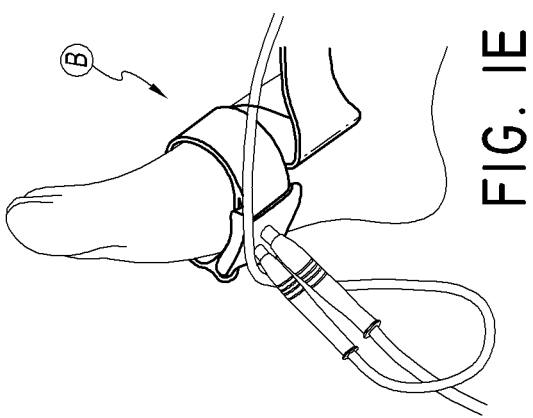
Figure 1G:
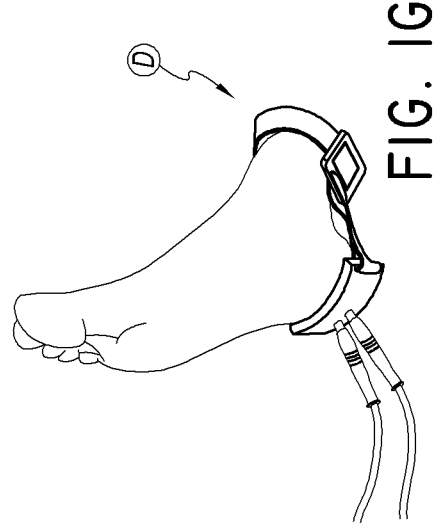
Figure 1D:
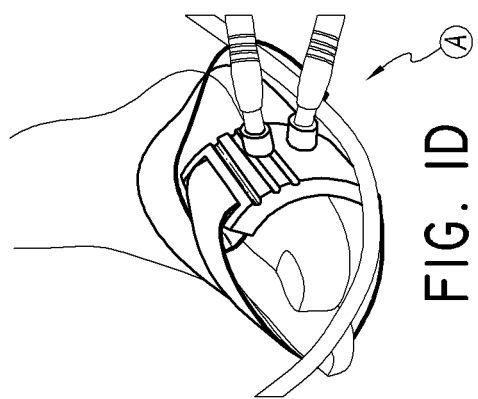

FIG. 1C is a branching diagram of the arteries supplying the pedal angiosomes. The blood flow measurement points A-E are illustrated as terminating respective artery branches, though in practice the measurement points need not be at the distal-most end of the respective arteries. As noted above, measurements at any of the points A-E may provide valuable clinical information regarding local perfusion.

Topographical-based peripheral vascular interventions, such as angiosome-directed peripheral vascular interventions, have been developed relatively recently, and show promising performance compared with traditional intervention, particularly in terms of improved limb salvage rates. A system employing a plurality of DOF sensors can provide real-time feedback on changes in perfusion of different topographical locations in the foot, e.g. angiosome by angiosome, so that interventional radiologists or vascular surgeons may immediately evaluate whether specific intervention at a target artery has succeeded in restoring sufficient blood perfusion to the targeted topographical region of the foot where the ulcer wound, ischemic tissue or other clinical manifestation is located.

Figure 2:
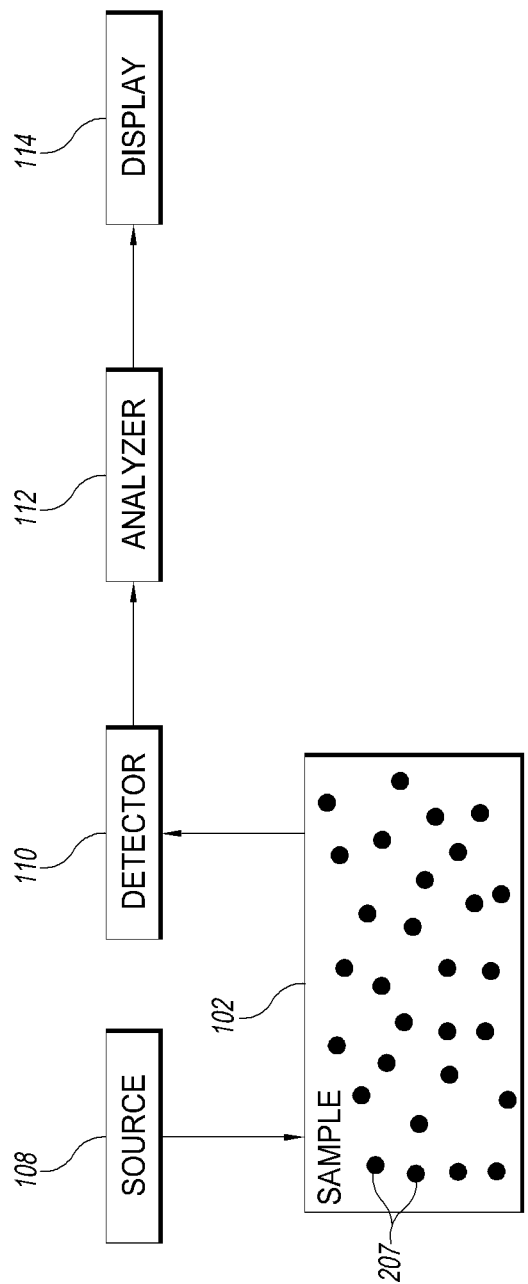
FIG. 2 is a block diagram of a system for measuring flow of turbid media.

FIG. 2 is a block diagram of a system for measuring flow of turbid media. A sample 102 includes a heterogeneous matrix therein. Within this matrix is an embedded flow layer with randomly ordered microcirculatory channels through which small particles 207 move in a non-ordered fashion. For example, in some embodiments the sample may be body tissue, with a complex network of peripheral arterioles and capillaries. A source 108 injects light into the sample 102. A detector 110 can detect light scattered by the moving particles 207 in the microcirculatory channels. The detector 110 can be positioned to receive light that passes from the source into the sample, and diffuses through the sample. In some embodiments, the detector can be coupled to the sample by a single-mode optical fiber. In some embodiments, the detector may be a multi-pixel image sensor, for example a CCD camera, used to image an area of the sample. In other embodiments, the detector may be a photon-counting avalanche photodiode (APD) or photomultiplier tube (PMT). As the particles flow in random direction, the scattering of light from the source 108 will vary, causing intensity fluctuations to be detected by the detector 110.

An analyzer 112 is coupled to detector 110 and configured to receive a signal from the detector 110. The analyzer 112 may comprise an autocorrelator, which measures the temporal intensity autocorrelation function of light received by the detector 110. The autocorrelation function can be used to obtain the scattering and flow characteristics of the small particles flowing in the sample 102. The time-dependent intensity fluctuations reflect the time-dependent density fluctuations of the small particles 207, and accordingly the autocorrelation function can be used to determine the flow rate within the sample 102. In some embodiments, a hardware autocorrelator may be employed, while in other embodiments a software autocorrelator can be used. The flow rate or other characteristic determined by the analyzer 112 may be outputted to a display 114. The measured quantity may therefore be provided to an operator via the display 114. In various embodiments, the operator may be a clinician, diagnostician, surgeon, surgical assistant, nurse, or other medical personnel. In some embodiments, the measurement may be provided via display 114 in substantially real-time. In some embodiments, the measurement may be provided via display 114 within about 1 second from measurement, e.g., within about 1 second of the time that the scattered light is detected by the detector, the measurement may be provided via display 114. In various embodiments, the measurement may be provided within less than about 10 minutes, within less than about 5 minutes, within less than about 1 minute, within less than about 30 seconds, within less than about 10 seconds, or within less than about 1 second from detection.

In some embodiments, as noted above, a software autocorrelator may be used. This may advantageously provide additional flexibility compared with a hardware autocorrelator, as it allows for data pre-processing. A software autocorrelator may also reduce the cost of a DCS system, while also reducing size and improving form factor. The ability to pre-process data can also improve the accuracy of measurements.

Figure 3:
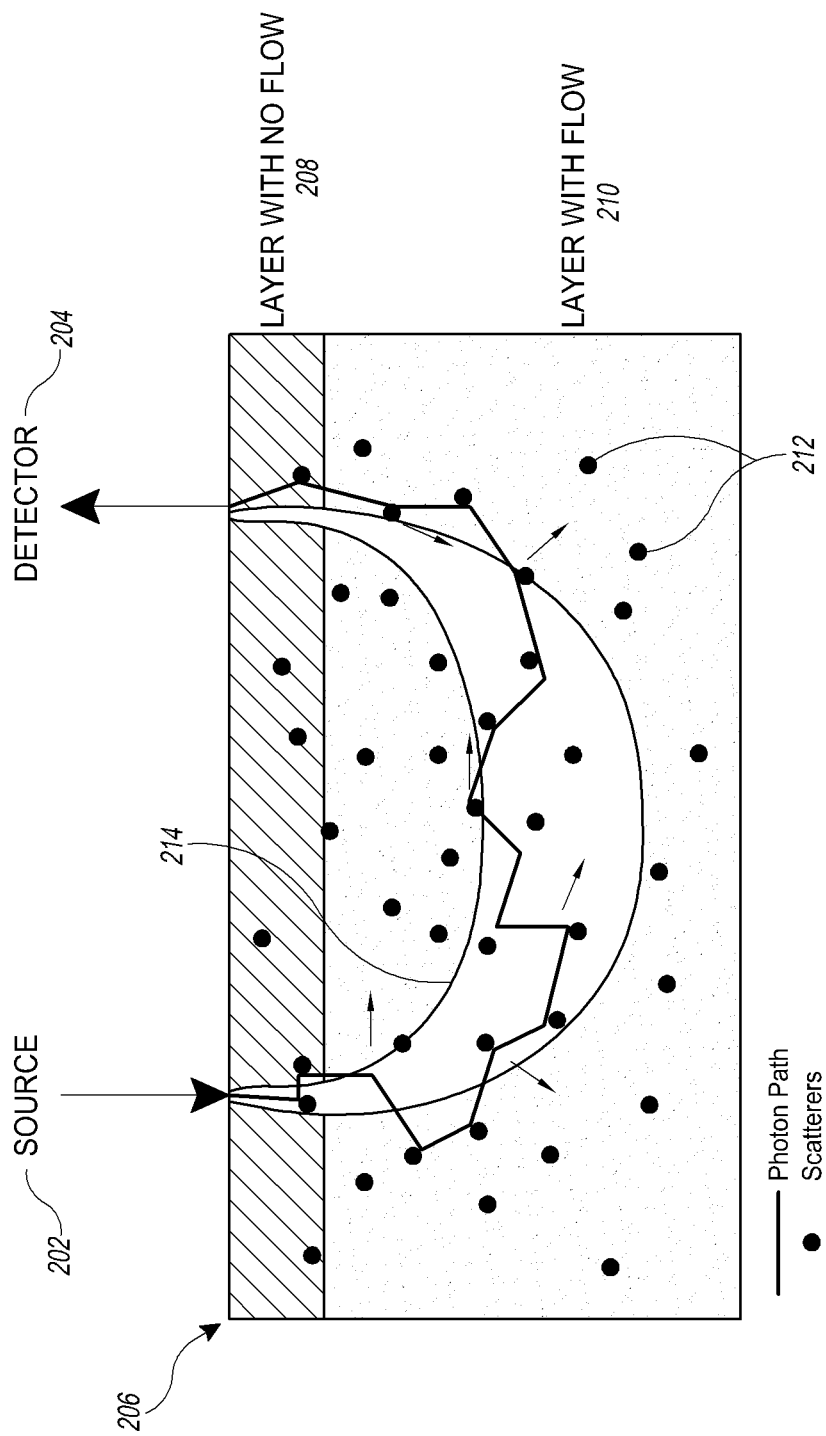
FIG. 3 is a schematic illustration of diffuse light penetration and detection in multi-layer tissue.
Figure 4:
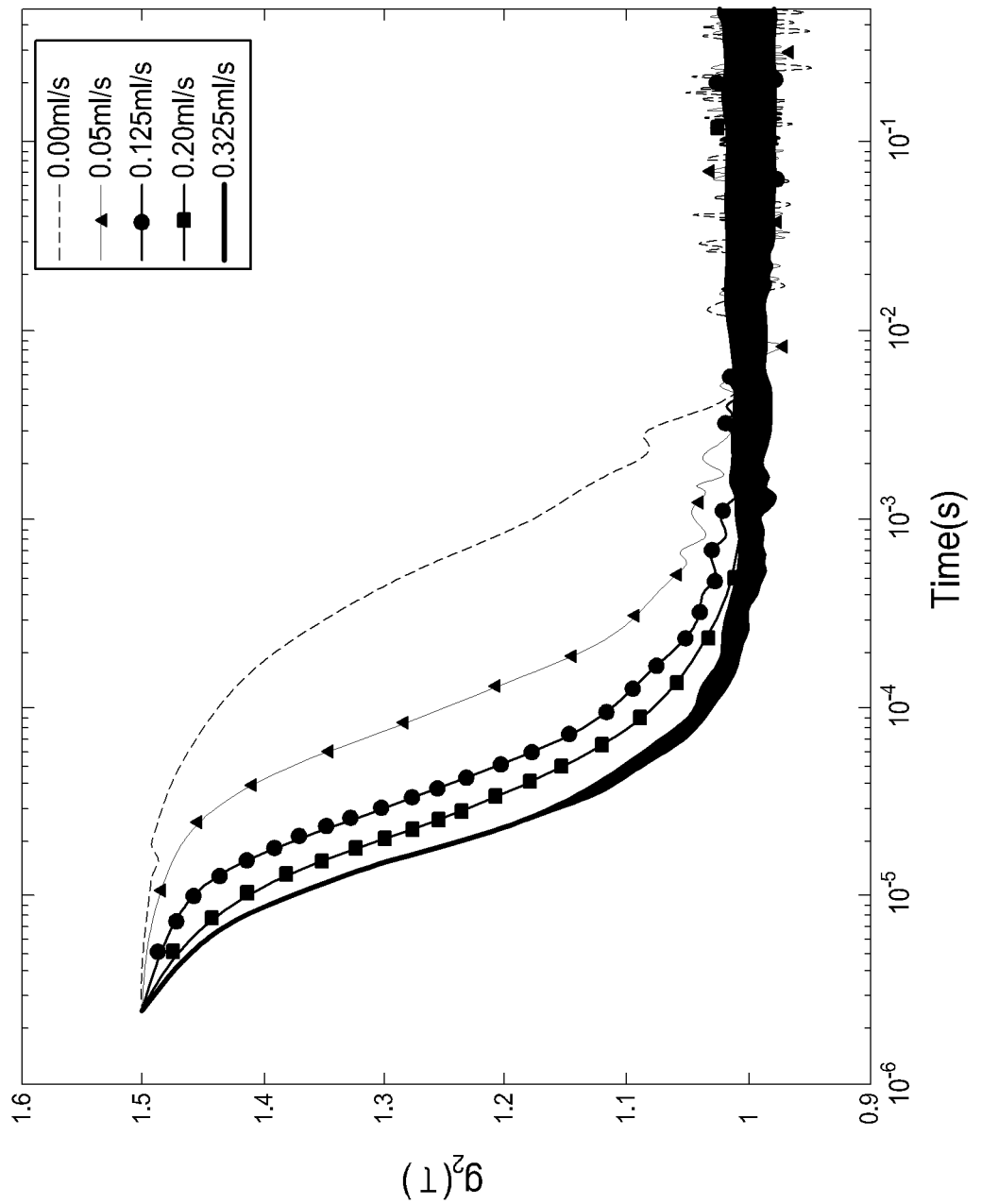
FIG. 4 is a graph of autocorrelation functions for different flow rates.

FIG. 3 is a schematic illustration of diffuse light penetration and detection in multi-layer tissue. As illustrated, a source 202 and a detector 204 are both positioned adjacent a portion of tissue 206. As noted above, in some embodiments optical fibers may be used to couple one or both of the source and detector to the tissue. The tissue 206 is multi-layer, including an upper layer 208 with no flow, and a deeper layer 210 with flow. A plurality of light-scattering particles 212 flow within capillaries in flow layer 210, and may include, for example, red blood cells. As light 214 is emitted from the source 202, it diffuses as it penetrates the tissue 206. As illustrated, a portion of the light 214 is diffused such that it is incident on the detector 204. The light 214 may follow a roughly crescent-shaped path from the source 202 to the detector 204. The depth of penetration of the light 214 detected by the detector 204 depends on the separation between the source and the detector. As the distance increases, penetration depth generally increases. In various embodiments, the separation distance may be between about 0.5 cm and about 10 cm, or in some embodiments between about 0.75 cm and about 5 cm. Preferably, in other embodiments the separation distance may be between about 1 cm and about 3 cm. In various embodiments, the separation distance may be less than about 10 cm, less than about 9 cm, less than about 8 cm, less than about 7 cm, less than about 6 cm, less than about 5 cm, less than about 4 cm, less than about 3 cm, less than about 2 cm, less than about 1 cm, less than about 0.9 cm, less than about 0.8 cm, less than about 0.7 cm, less than about 0.5 cm, less than about 0.4 cm, less than about 0.3 cm, less than about 0.2 cm, or less than about 0.1 cm. The penetration depth may vary, for example in some embodiments the penetration depth of the sensor may be between about 0.5 cm and about 5 cm, or in some embodiments between about 0.75 cm and about 3 cm. Preferably, in other embodiments the penetration depth may be between about 5 mm and about 1.5 cm. Of course, the tissue optical properties of the various layers also contribute to the penetration depth of the light, as does the intensity, wavelength, or other characteristics of the light source. These variations can allow for the depth of measurement to be adjusted based on the part of the body being analyzed, the particular patient, or other considerations. Measurements obtained by the detector 204 may then be processed and analyzed to calculate the autocorrelation function. As seen in FIG. 4, the autocorrelation function may be used to determine the flow rate in the tissue.

FIG. 4 is a graph of autocorrelation functions for different flow rates, with steeper decay of the autocorrelation curve indicating faster flow rates. The autocorrelation curves are plotted on a semi-logarithmic scale in the graph. As is generally known in the art, blood flow data can be analyzed by fitting each autocorrelation curve to a model, such a semi-infinite, multi-layer diffusion model. The fitted autocorrelation curves can then provide relative blood flow rates, which can be usefully applied during peripheral interventional procedures such as balloon angioplasty or surgery, or as a diagnostic tool.

Diffuse optical flow (DOF) sensors (which, as described above, can include either or both DCS and DSCA sensors) can be particularly useful in measuring microcirculation, for example in measuring blood perfusion in the foot. This technique can be additionally improved by employing the concept of pedal topography. One example of a topographical analysis of blood flow in the foot incorporates the concept of pedal angiosomes, as described above.

In many cases, prior to vascular intervention, an interventional radiologist or vascular surgeon will image the vasculature of interest, for example using fluoroscopy, computed tomography, ultrasound, or other imaging technique. With such imaging, several potential occlusions or lesions may be identified. Peripheral intervention, such as balloon angioplasty, atherectomy, or surgical bypass/grafts can be employed to re-open one or more of the identified occlusions or lesions ("the target lesions"), in an effort to restore perfusion to the affected region(s) of the foot. For these peripheral interventions to result in successful limb salvage, blood perfusion must reach a sufficient level that permits healing of the foot wound. Without a real-time perfusion monitor, a physician has no way of knowing for sure if an intervention has achieved an improvement in perfusion sufficient for wound healing, or at all. The use of real-time measurement of blood perfusion at various topographic locations of the foot, as described herein, addresses this problem. It provides objective quantitative perfusion data in real-time so that the physician can know with certainty whether a specific intervention at a target lesion has succeeded in restoring perfusion to the topographic region of the foot on which the wound is located. If a determination has been made that an acceptable level of perfusion at the desired topographic region has been achieved, the physician can avoid the additional risk associated with further intervention, and bring the procedure to a close. Alternatively, if a specific intervention at a target lesion has not resulted in any perfusion improvement as measured by a real-time perfusion monitor, the physician will thereby be guided to undertake the additional risk of proceeding onto secondary target lesions. The use of a real-time perfusion monitor thus averts the situation where a peripheral intervention procedure is ended prematurely prior to achieving the desired improvement in perfusion. It also guides physicians as to which target lesion (when revascularized) resulted in the greatest perfusion improvement at the desired topographic region of the foot. This real-time knowledge would in turn inform the physician as to the optimal placement for use of a drug-eluting balloon or other means to prolong the patency of the vessel in which the said lesion is located.

Figure 5A:
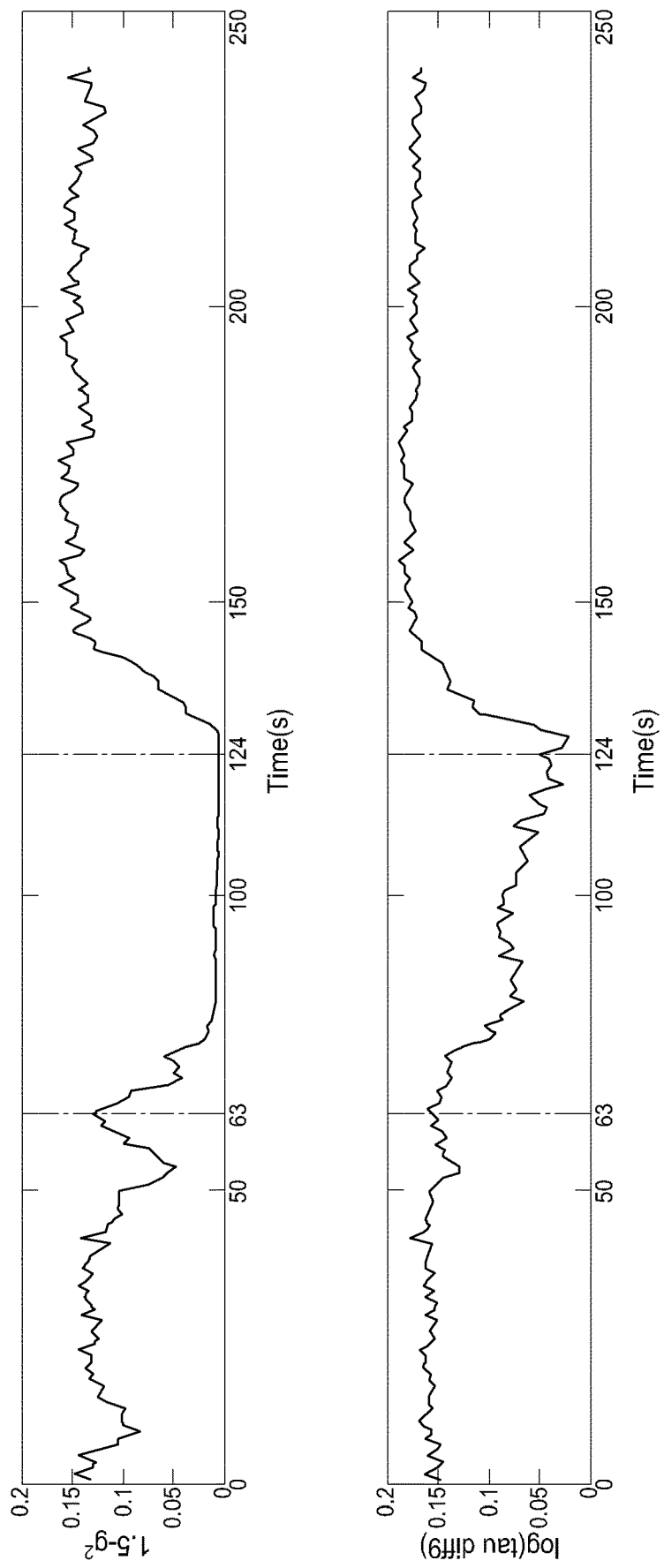
FIG. 5A is a graph of two blood flow indices (BFIs) during cuff occlusion protocol.
Figure 5B:
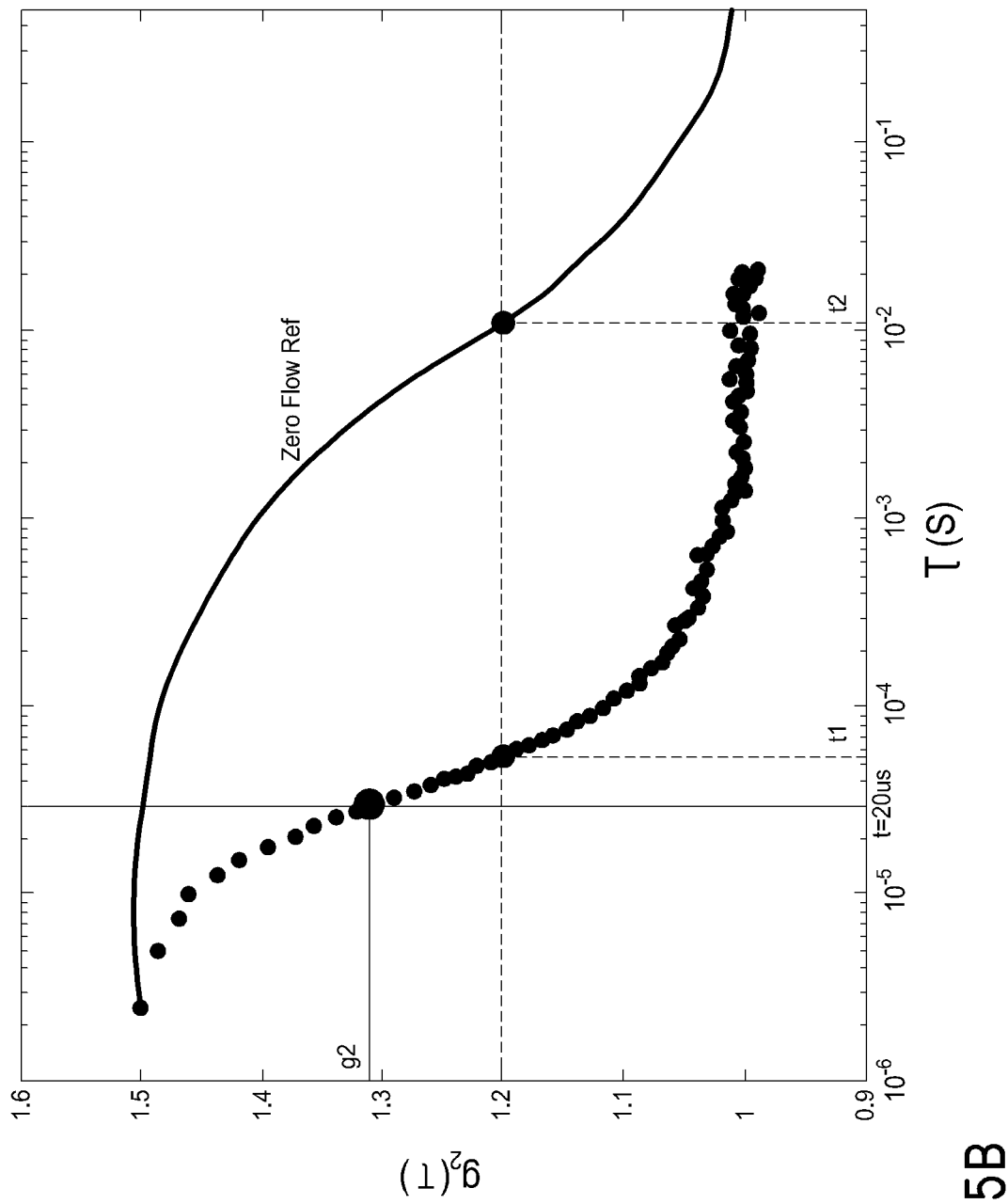
FIG. 5B is a graph of autocorrelation functions illustrating the derivation of the two BFIs of FIG. 5A.

Although changes in perfusion can be seen directly from the change in shape of the autocorrelation function, potentially more useful ways to define a blood flow index (BFI), which may also be referred to herein as a blood perfusion index (BPI) have been developed. FIG. 5A is a graph of two such BFIs over time during a cuff occlusion protocol. The dashed vertical lines indicate the starting and stopping times of the cuff inflation. The top chart illustrates a BFI calculated from vertical crossing of the autocorrelation curve, while the lower chart illustrates a BFI calculated from horizontal crossing of the autocorrelation curve. FIG. 5B is a graph illustrating these two different methods of calculating BFI. The solid line represents the zero flow reference data, while the dotted line represents real-time autocorrelation data. The vertical crossing indicator compares the y-axis value ($g_2$) of the real-time autocorrelation data and the reference data at a given time. For example, the first indicator can be calculated as $1/g_2$ or $1.5-g_2$. The horizontal crossing indicator compares the time difference between the autocorrelation data and the reference data at a given flow rate. For example, the second indicator can be calculated as $\log(t2/t1)$.

Charts such as those shown in FIG. 5A, or other such indicia of blood flow, can be displayed to an operator in real-time via audible, visual, or tactile feedback. A physician may thereby be provided with substantially real-time feedback on the efficacy of a peripheral intervention. For example, during balloon angioplasty, a physician can monitor the BFI as measured on a specific location of the foot. The BFI will decrease while the balloon is inflated, and increase after deflation. After repeated inflation of the balloon to perform the angioplasty, the BFI should increase relative to the pre-angioplasty baseline, indicating that the angioplasty procedure has resulted in an improvement in perfusion at the target foot tissue. A BFI that does not increase relative to the pre-angioplasty baseline indicates that the balloon angioplasty was not successful in restoring perfusion. Providing such feedback in real-time is an enormous benefit to physicians performing vascular intervention. Rather than waiting post-operatively for hours or days to determine whether perfusion has been improved, during which time the foot may deteriorate to the point of requiring amputation, the use of DOF sensors at select pedal locations during the angioplasty procedure can provide immediate feedback, allowing the physician to continue, modify, or conclude the procedure as needed. As noted above, in various embodiments, the feedback may be provided, in some cases, within less than about 10 minutes, within less than about 5 minutes, within less than about 1 minute, within less than about 30 seconds, within less than about 10 seconds, or within less than about 1 second from measurement. In some embodiments, success of a revascularization procedure can be indicated by an increase in BFI of about or at least about 5%, 10%, 15%, 20%, 25%, 30%, 35%, 40%, 45%, 50%, 55%, 60%, 65%, 70%, 75%, 80%, or more compared to a BFI value prior to the procedure.

While the example above relates to balloon angioplasty, the use of DOF sensors to assess blood flow (whether relative, absolute, or both) in the foot can be advantageously applied before, during, or after a number of different interventions. For example, DOF sensors can be used to aid interventions such as rotational atherectomy, delivery of lytic substances including but not limited to tPA, bypass procedures, stent and/or graft placement, or any other intervention.

In addition to the above-described real-time monitoring of blood perfusion in the operating room, derivative indices based on the raw blood perfusion data generated via DCS or DSCA can also serve as tools in an inpatient or outpatient setting, for example, to direct appropriate wound or ulcer therapy based on the patient's level of tissue perfusion, or to screen for critical thresholds of peripheral arterial disease, by measuring blood perfusion in the extremities (e.g. the foot). Such derivative indices include the Foot Thumb Index ("FTI"), the Low Frequency Oscillation Index ("LFI") and its two parameters of "$LFI_A$" and "$LFI_M$", as well as the Support Vector Machines Index ("SVM") and the Flow Transform Level ("FTL"). These derivative indices are described below and will jointly be referred to as "the Derivative Indices." In some embodiments, the function of time references in one or more of the derivative indices can be, for example, between about 15 seconds and about 15 minutes, between about 30 seconds and about 5 minutes, between about 30 second and about 2 minutes, or about 30 seconds, 45 seconds, 1 minute, 1.5 minutes, 2 minutes, 2.5 minutes, 3 minutes, 4 minutes, 5 minutes, 6 minutes, 7 minutes, 8 minutes, 9 minutes, 10 minutes, or ranges involving any two of the foregoing values.

The Foot-Thumb Index ("FTI")

As described elsewhere in this application, blood flow measurements may be made via absolute BFI measurements, or relative BFI readings before and after an intervention, for example, before and after angioplasty, such as balloon angioplasty. However, an alternative measurement of perfusion may be obtained by taking the ratio of the absolute BFI in the foot to the absolute BFI in another reference location on the body such as but not limited to the thumb, earlobe, upper arm (deltoid/shoulder region), or palm (thenar eminence). For ease of reference, this alternative measurement is referred to herein as the FTI (the Foot-Thumb Index).

The FTI may address the difficulty in comparing absolute BFI readings from one individual to another given the variability occasioned by different physiological and environmental factors such as room temperature, skin/tissue temperature, hemoglobin concentration, time of day, skin pigmentation, etc. It thus allows for calibration towards a standardized value or range of values that serves as basis for differentiating ischemic and non-ischemic tissue. This standardization would provide reference values for populations, both normal and abnormal, and do so without the need for standardized temperature or environmental pressure which is required for laser Doppler or transcutaneous oxygen measurements.

Figure 6:
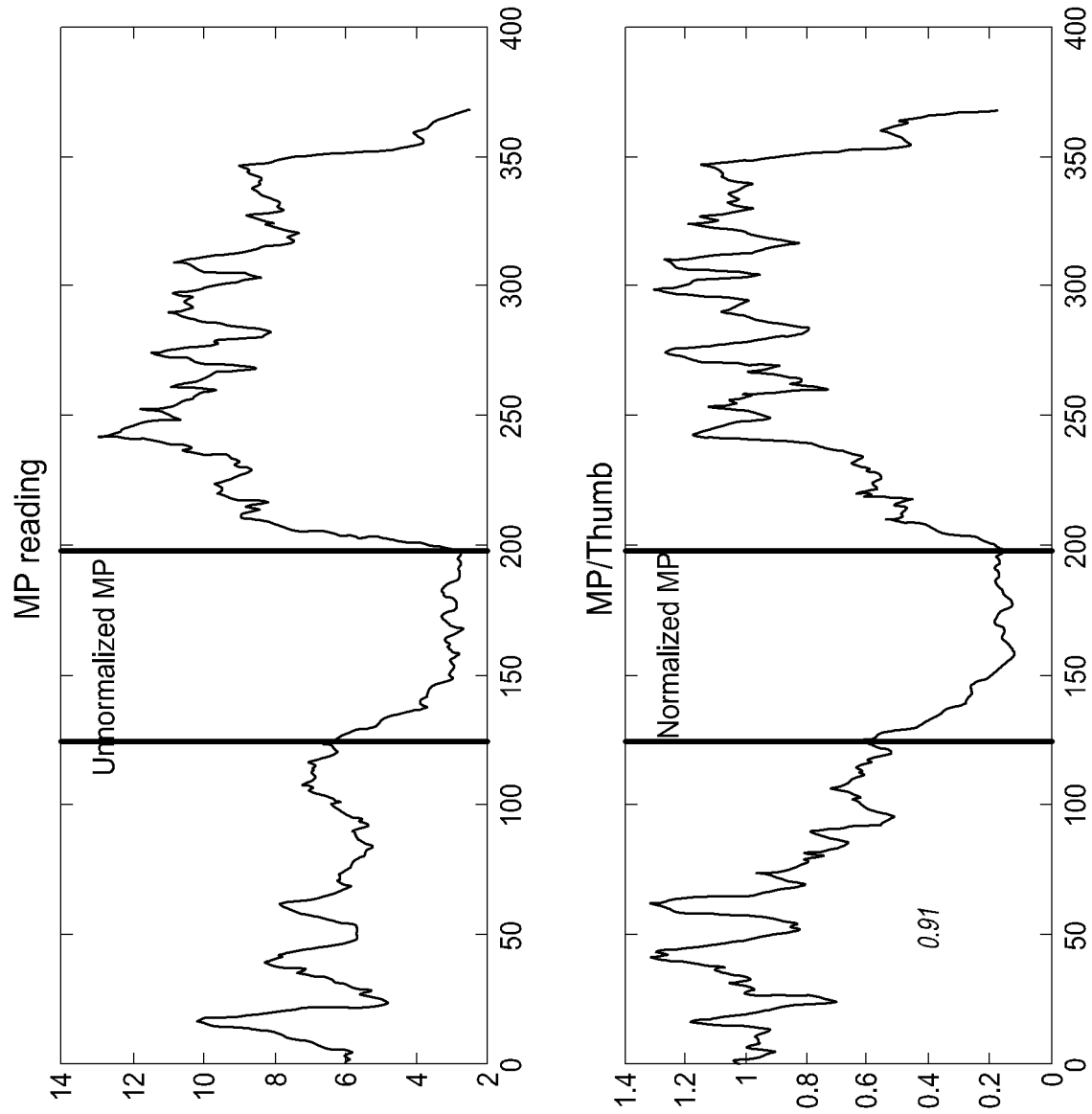
FIG. 6 is a graph of two BFIs during cuff occlusion protocol.

With reference to FIG. 6, the upper chart illustrates the relative BFI chart reflecting perfusion in the medial plantar angiosome of the foot of an individual undergoing a cuff occlusion, as measured by DSCA, with the cuffed period marked out between the vertical lines. The lower chart illustrates the FTI or medial plantar BFI normalized against the thumb BFI of the same patient during the cuff occlusion process. As shown in FIG. 6, the unnormalized values reflect the absolute BFI readings while the FTI (normalized) value (between the two vertical markers) reflects the FTI during the cuffed period. The 0.91 listed in FIG. 6 refers to the mean of the BFI prior to cuff occlusion (to the left of the first vertical line).

In some embodiments, comparing the calculated FTI to a predetermined threshold value is utilized to discriminate between a first population (e.g., a population having a characteristic disease or risk factor for the characteristic disease, e.g., an ischemic population) and a second population (e.g., a population not having a characteristic disease or risk factor for that characteristic disease, e.g., a non-ischemic population; or a different disease or risk factor for the different disease). In some embodiments, it can be determined that a subject falls into a characteristic population, e.g., an ischemic population, if the FTI is less than about 0.90, 0.88, 0.86, 0.84, 0.82, 0.80, 0.78, 0.76, 0.74, 0.72, 0.70, 0.68, 0.66, 0.64, 0.62, 0.60, 0.58, 0.56, 0.54, 0.52, 0.50, 0.48, 0.56, 0.54, 0.52, 0.50, 0.48, 0.46, 0.44, 0.42, 0.40, or less.

Low Frequency Oscillation Index ("LFI")

LFI is a measurement index related to LFO, the low frequency oscillation observed in hemodynamic measurements such as blood flow, oxygenation, volume and pressure. The current literature describes two different origins of LFO, namely those derived from Mayer waves and vasomotion waves. Mayer waves are spontaneous oscillations in arterial pressure, which oscillations have significant correlation with oscillations of sympathetic nerve activity. Vasomotion waves, on the other hand, are oscillations generated by the blood vessel walls. The key distinction is that Mayer waves are driven by nerve activity while vasomotion waves are a characteristic of the vessel wall's autonomic behavior which is not correlated to nerve activity.

Similar observations have been made in earlier studies, albeit with more rudimentary laser Doppler tools (Schmidt et al, J Vasc Surg 1993; 18:207-15 and Stansberry et al, Diabetes Care; July 1996; 19, 7: 715-21). In the context of blood flow, oscillations caused by vasomotion can be measured by laser Doppler flowmetry, but only in small spatial scale. In clinical parlance, this means that laser Doppler cannot penetrate beyond skin level to measure tissue perfusion at depth. With the development of diffuse speckle contrast analysis (DSCA) which can utilize a CCD as a detector to integrate transmitted light intensity, coupled with statistical analysis to retrieve minute blood flow data, it is now possible to overcome the limitations of laser Doppler to measure LFO at tissue depths up to two centimeters, or greater in some embodiments. Relative to laser Doppler, the tissue volume measured in DSCA is several orders of magnitude larger, and hence the observed LFO is much more sensitive to microcirculatory pathologies.

Studies by Rucker et al (Rucker et al in Am J Physiol Heart Circ, 2000) showed that under critical perfusion conditions (when arterial blood supply is reduced to the point of ischemia), it is the vasomotion and flow motion in the skeletal muscle that preserve nutritive function to surrounding tissue like skin, subcutis and periosteum, which are incapable or less capable of this protective mechanism. In addition, the impaired endothelial dysfunction as seen in diabetes directly impairs vasomotor function (Kolluru et al in Intl J of Vascular Med 2012) leading to delayed vascular re-modeling and wound healing. It follows therefore that measurement of either just partial pressure of oxygen ($TcPO_2$) or perfusion pressure in the skin alone (SPP) do not reflect the critical nature of the ischemia in the underlying tissue to be able to predict wound healing accurately. LFO evaluation of deep tissue perfusion (e.g., up to 2 cm) is a direct measure of microvascular vasomotor function in tissue and is likely to be a superior predictor of wound healing.

The impact of these underlying pathologies also explains the significant correlation between the Derivative Indices and ischemia. In healthy patients, there a larger deviation and variance in blood perfusion owing to healthier and more elastic vessels. Also, their cardiovascular function is likely to be stronger and as a consequence causing larger variation in blood perfusion. In contrast, patients with ischemia may have a variety of co-morbidities including diminished cardiac capacity and calcified microvasculature resulting in less exuberant blood perfusion fluctuations.

As described in more detail above as well as in U.S. Pub. No. 2014/0052006 A1, which is hereby incorporated by reference in its entirety, optical measurement techniques such as diffuse speckle contrast analysis (DSCA) can be utilized to measure real-time blood perfusion in tissue depths of up to two centimeters (2 cm), in absolute BFI ("blood flow index") units. The BFI readings, however, do not represent the full extent of the information that can be obtained from the raw data. In addition to BFI, it is possible to extract critical information about the health of the microvascular blood vessels by evaluating characteristics of the BFI signal, including, but not limited to, analyzing the BFI signal's power spectrum and statistical characteristics.

DSCA Measurements in Healthy v. Ischemic Feet

The BFI measurement of blood perfusion was taken of 68 individuals from two groups. The first group comprised 30 healthy volunteers, while the second group comprised 38 patients who sought treatment for claudication, amputation follow-up or general podiatry. Of the healthy volunteers, 4 were excluded due to BMI>28. For the patient group, 2 were excluded due to incorrect fiber connection of the equipment, 2 were excluded for known venous disease, and 8 were excluded due to normal readings of ankle-brachial index (ABI) and/or toe-brachial index (TBI), coupled with physician assessment of a lack of clinical indicators of ischemia, or the presence of clinical indicators that pointed away from ischemia. The resulting data was thus based on a comparison of 26 measurements in the healthy group, and 26 measurements in the patient group.

In the healthy group, there were 11 men plus 15 women, with an age range between 22 to 46, and a median age of 31. In the patient group, there were 14 men plus 12 women, with an age range between 53 and 82, and a median age of 68.

Data Acquisition

Figure 7:
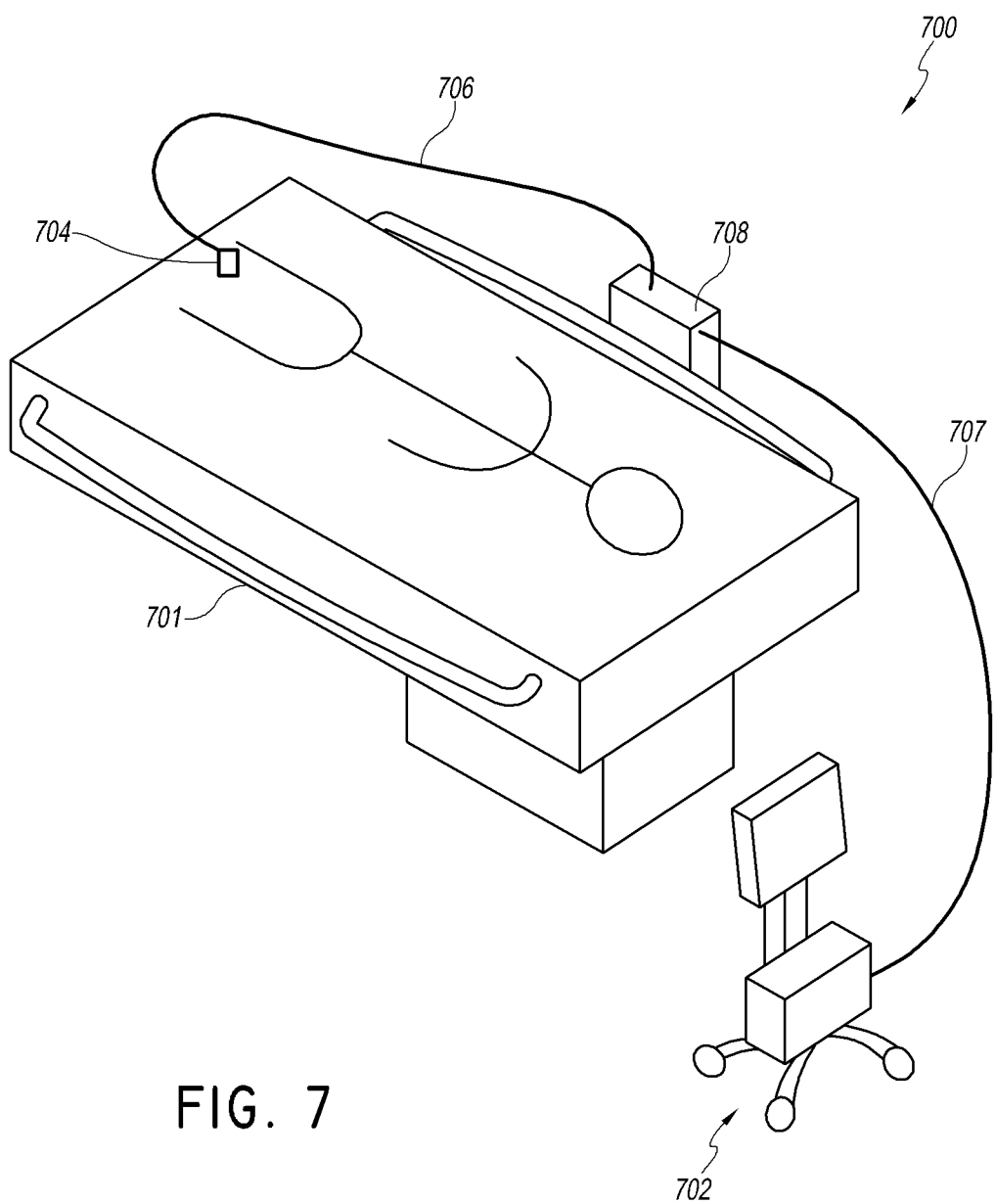
FIG. 7 illustrates various elements of a perfusion monitoring system, according to some embodiments.

In some embodiments, a system for blood flow assessment includes a support structure configured to be positioned on an anatomical location of a patient, one or more sensors carried by the support structure, an analyzer configured to analyze data from the sensor(s) to determine absolute and/or relative blood flow at a location near the sensor, and a feedback device configured to provide a signal indicative of the absolute and/or relative blood flow determined by the analyzer. In some embodiments, as illustrated in FIG. 7, a system 700 may be arranged in a distributed configuration comprising at least two sub-sections such as a console 702 disposed on a movable cart, with an extension umbilical adaptor 708 that is connected to the catheterization table 701. The umbilical adaptor 708 will be configured to connect (e.g., via sensor leads 706) with patient contacting sensors 704, and can also connect via conduit 707 to the console 702. Placing the umbilical adaptor 708 in proximity to the patient on the catheterization table 701 can simplify the connection/disconnection of sensors 704 to/from the system, and simplify the application of the sensors 704 to the patient. Any of the connections described and illustrated can be wired or wireless connections. The umbilical adaptor 708 may be passive—providing only a remote connection point for patient contacting sensors 704; or may be active—comprising active circuitry and optics, which may include (but is not limited to) sensor detection, identification, authentication hardware/software; contact verification hardware/software; one, two, or more laser sources (e.g., 1, 2, 3, 4, 5, or more laser sources); one, two, or more photodetectors (e.g., 1, 2, 3, 4, 5, or more photodetectors); CPU; display; touchscreen; keyboard/buttons; audio/visual annunciators; power source; data storage; wireless/wired/optical networking interfaces; input/output connectors/interfaces; gesture recognition interface, and the like. The console 702 can include active circuitry and optics, which may include (but is not limited to) sensor detection, identification, authentication hardware/software; contact verification hardware/software; one, two, or more laser sources (e.g., 1, 2, 3, 4, 5, or more laser sources); one, two, or more photodetectors (e.g., 1, 2, 3, 4, 5, or more photodetectors); CPU; display; touchscreen; keyboard/buttons; audio/visual annunciators; power source; data storage; wireless/wired/optical networking interfaces; input/output connectors/interfaces; gesture recognition interface, and the like.

The patient contacting sensors may be configured as single (one-time) use disposables or multiple use devices. Single use enforcement may be implemented using methods including, but not limited to, time-limited activation based on unique serial numbers on packaging, procedure limited activation based on embedded identification circuitry, frangible connectors, frangible patient contacting assemblies, light/time/air sensitive materials which degrade mechanically, chemically, or optically, keyed resistance/impedance circuits, custom keyed connectors, or any anti-counterfeiting method that may be appropriately adapted for this application, or any combination thereof.

Figure 7A:
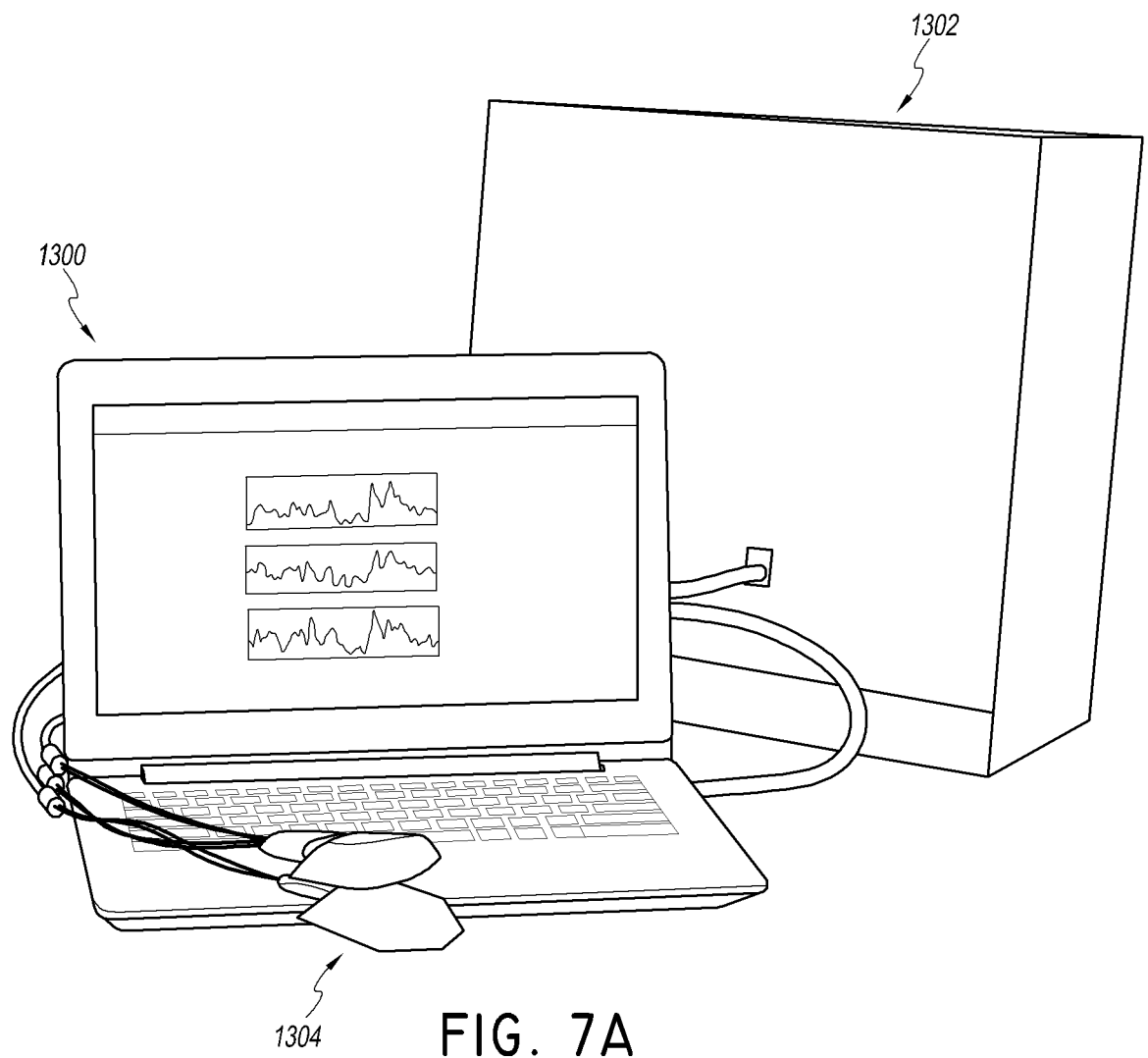
FIG. 7A illustrates an embodiment of a DSCA perfusion monitor console and instrumentation box.
Figure 7B:
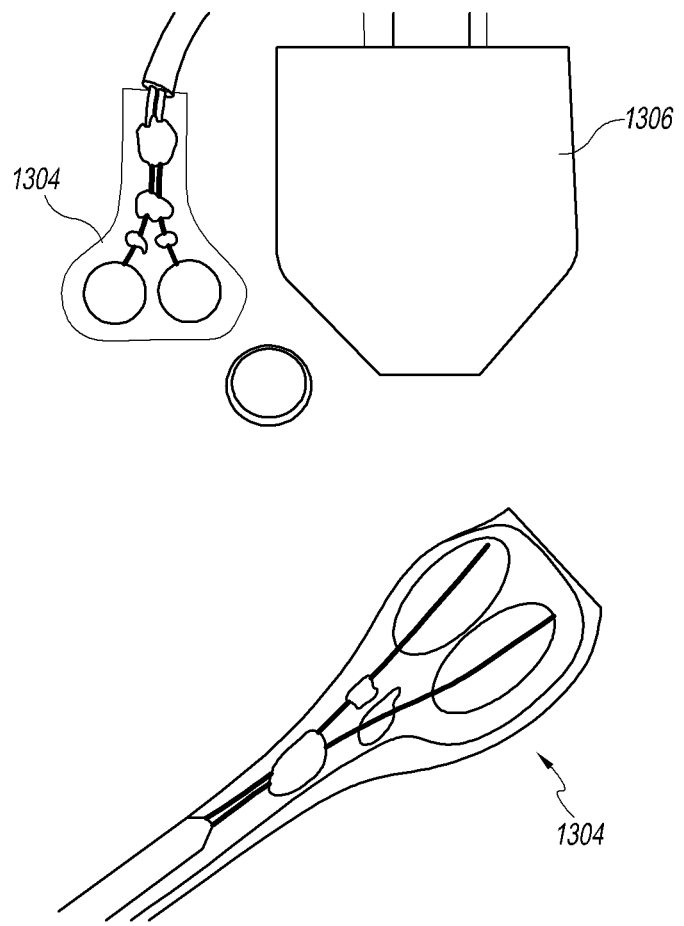
FIG. 7B illustrates embodiments of low-profile sensors.

The instrument used for measurement of BFI and LFO can be, for example, a DSCA perfusion monitor, which may be a 3-channel monitor in some embodiments. Each of the 3 channels can be connected via a laser fiber to a sensor comprising a laser source and detector. FIGS. 7A-7C show one embodiment of the device and the low-profile sensors 1304 attached to the foot via adhesive Tegaderm tape 1306 (3M, United States). FIG. 7A illustrates an embodiment of the console 1300 and instrumentation box 1302. FIG. 7B illustrates embodiments of low-profile sensors 1304.

Each volunteer/patient was asked to sit while sensor locations were identified on the medial plantar and calcaneal areas of the foot, avoiding calluses, and on the deltoid of the arm. Local temperature readings were taken at the medial plantar, calcaneal and deltoid using a non-contact dermal imager (Ti9, Fluke Corporation). One sensor was then affixed to each of the medial plantar, calcaneal and deltoid. Once the three sensors were affixed, the BFI data was recorded for 5 minutes with the patient in a seated position with both feet hanging down. Thereafter, the patient was asked to lie down in a supine position and the BFI data was recorded for another 5 minutes. Finally, the sensors were detached, and temperature on the three sites was taken one more time. All readings were taken on the right side of the body, unless the right foot or forefoot had already been amputated, or where the patient presented with clinical evidence of greater ischemia on the left leg as compared to the right e.g., a chronic non-healing wound on the left foot, extreme claudication on the left leg with no symptoms on the right, angiographically defined vessel narrowing in the left limb vessels, etc.

Power Spectrum Analysis:

The 5 minute time-series BFI data of patients in supine positions at a sampling frequency of 1 Hz (total data set was 300 points) was normalized by dividing it by its mean value, and then subjected to a Fast Fourier Transformation to obtain the Power Spectrum.

Figure 8A:
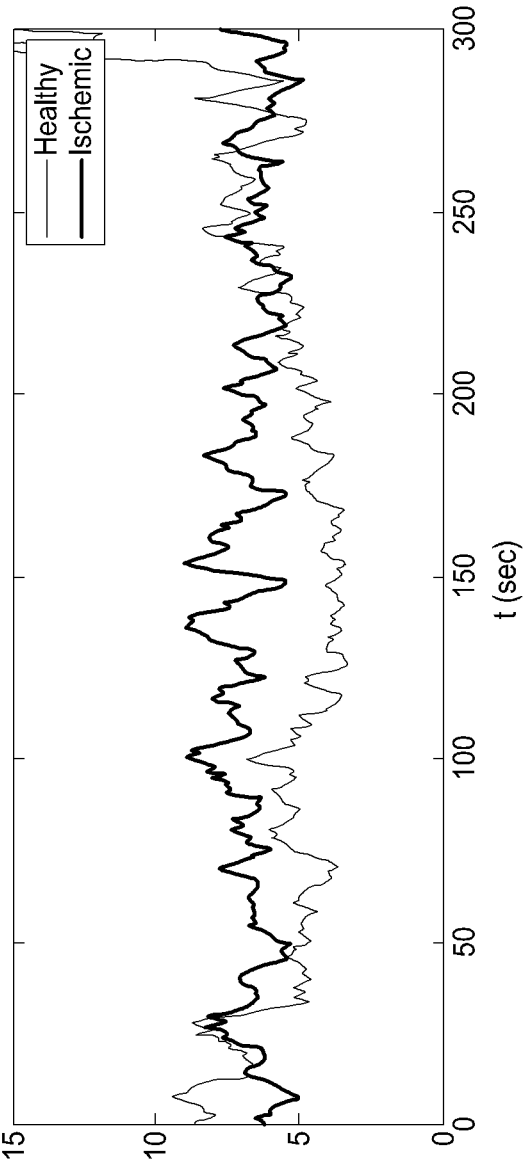
Figure 8B:
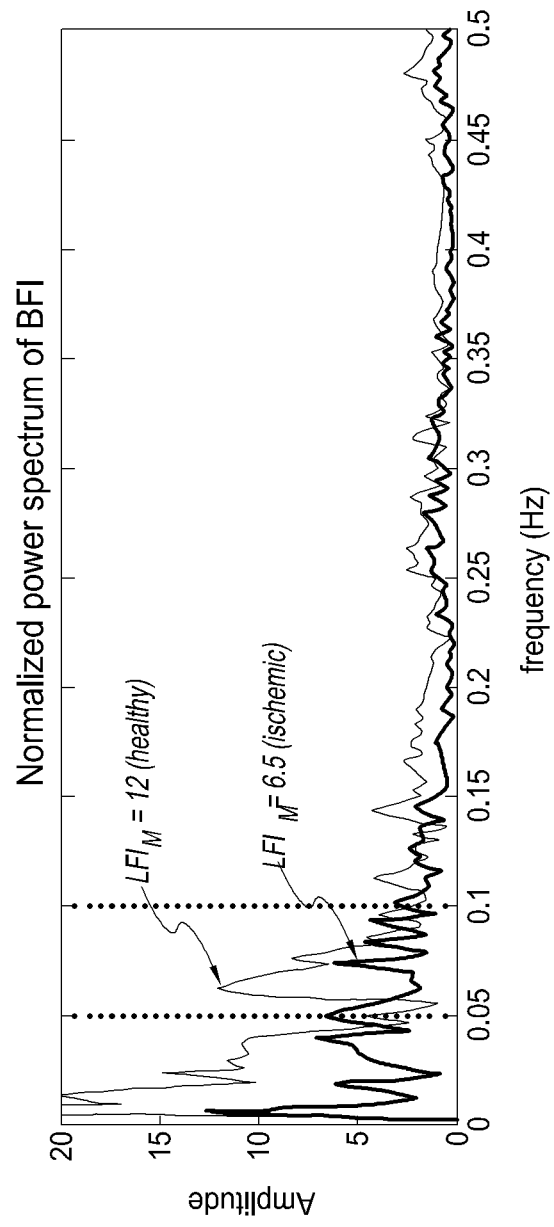
FIG. 8B shows the equivalent power spectrum data of the same individuals (Fourier transform of raw time series BFI data.

By way of example, FIG. 8A shows the raw BFI data (raw time series BFI data) measured at the medial plantar section of the foot of two individuals, one healthy versus one with indications of limb ischemia, while FIG. 8B shows the equivalent power spectrum data of the same individuals (Fourier transform of raw time series BFI data. Low frequency oscillation indices based on maximum peak signal ($LFI_M$) are shown with arrows).

There are several parameters/characteristics that can be obtained from the Power Spectrum, and a few examples are listed in the table below:

TABLE 1

Examples of parameters that can be derived/extracted from BFI Power Spectra.

| | |
|---|---|
| $LFI_M$ | The Low Frequency oscillation Index (Maximum) relates to the peak signal power in the frequency band between 0.045 Hz and 0.1 Hz |
| $LFI_A$ | The Low Frequency oscillation Index (Area) relates to the area under the normalized spectrum in the frequency band between 0.045 Hz and 0.1 Hz |
| Absolute Power: | The Absolute Power of a frequency band, $P_A(f_L, f_H)$, is defined as the signal power within that specific frequency band from $f_L$ to $f_H$. Mathematically: If a signal x(t) has Fourier transform X(f), its power spectral density is $|X(f)|^2 = Sx(f)$. The absolute spectral power in the band of frequencies from $f_L$ Hz to $f_H$ Hz is given by $$\text{Absolute Spectral Power in Band} = \int_{fL}^{fH} Sx(f)df$$ |
| Relative Power: | The Relative Power, $P_R(f_L, f_H)$, of a frequency band is defined as the ratio of the absolute power within that specific frequency band (from $f_L$ to $f_H$) divided by the total signal power across the entire frequency spectrum. This is a dimensionless quantity. $P_R(f_L, f_H) = P_A(f_L, f_H)/P_A(0, \infty)$ Mathematically: The relative spectral power measures the ratio of the total power in the band (i.e., absolute spectral power) to the total power in the signal, i.e., |

TABLE 1-continued

Examples of parameters that can be derived/extracted from BFI Power Spectra.

$$\text{Relative Spectral Power in Band} = \frac{\int_{fL}^{fH} Sx(f)df}{\int_{0}^{\infty} Sx(f)df}$$

| | |
|---|---|
| Band-Pass Correlation Coefficient: | Band-pass filtering refers to the processing the original time series data to extract signal components that exists within a specific frequency band. For example, a 0.01 Hz to 0.1 Hz band-pass filter will only allow signal components between 0.01 Hz to 0.1 Hz to pass; signal components frequencies lower than 0.01Hz or higher 0.1 Hz will be blocked.<br>The Pearson correlation coefficient between two variables is defined as the covariance of the two variables divided by the product of their standard deviations. The result is a number between +1 and −1, where 0 represents that there is no correlation, and +1 or −1 represent complete positive or negative correlations respectively. For example, a correlation coefficient can be calculated between the time series BFI data from two separate anatomical regions of the same patient (e.g. calcaneal BFI correlation with medial plantar BFI), which will provide a measure of how similar the two signals are.<br>-pass filters are known, such as the 3rd order Butterworth filter etc. The band-pass correlation coefficient of two signals is the Pearson correlation coefficient calculated between two signals that have undergone band-pass filtering. For example, one can calculate the correlation coefficient between arm and medial plantar BFI signals that have been band-pass filtered. |

One Dimensional Data Analysis of Power Spectrum

Two parameters for one-dimensional analysis of the Power Spectrum were evaluated, based on the Low Frequency Oscillation Index ("LFI") characteristics within the frequency band between 0.045 Hz and 0.10 Hz, and are described above. $LFI_M$ is defined as the maximum amplitude in the 0.045-0.10 Hz frequency band, and assumes that most of the low frequency oscillation (LFO) signals are explained by one single peak within the LFO frequency range of 0.045 to 0.10 Hz. In another words, it assumes that the frequency of the LFO signal does not vary appreciably during 5 minutes of data acquisition time. In contrast, $LFI_A$ is defined as the area under the curve within the 0.045-0.10 Hz frequency band, is a more suitable metric if one assumes that the frequency of LFO changes significantly within this frequency range during the acquisition time. In some embodiments, other frequency bands can be utilized for a particular index depending on the desired clinical result. For example, the frequency in some embodiments could be less than 0.15 Hz, or less than about 0.10 Hz.

Results

Figure 9A:
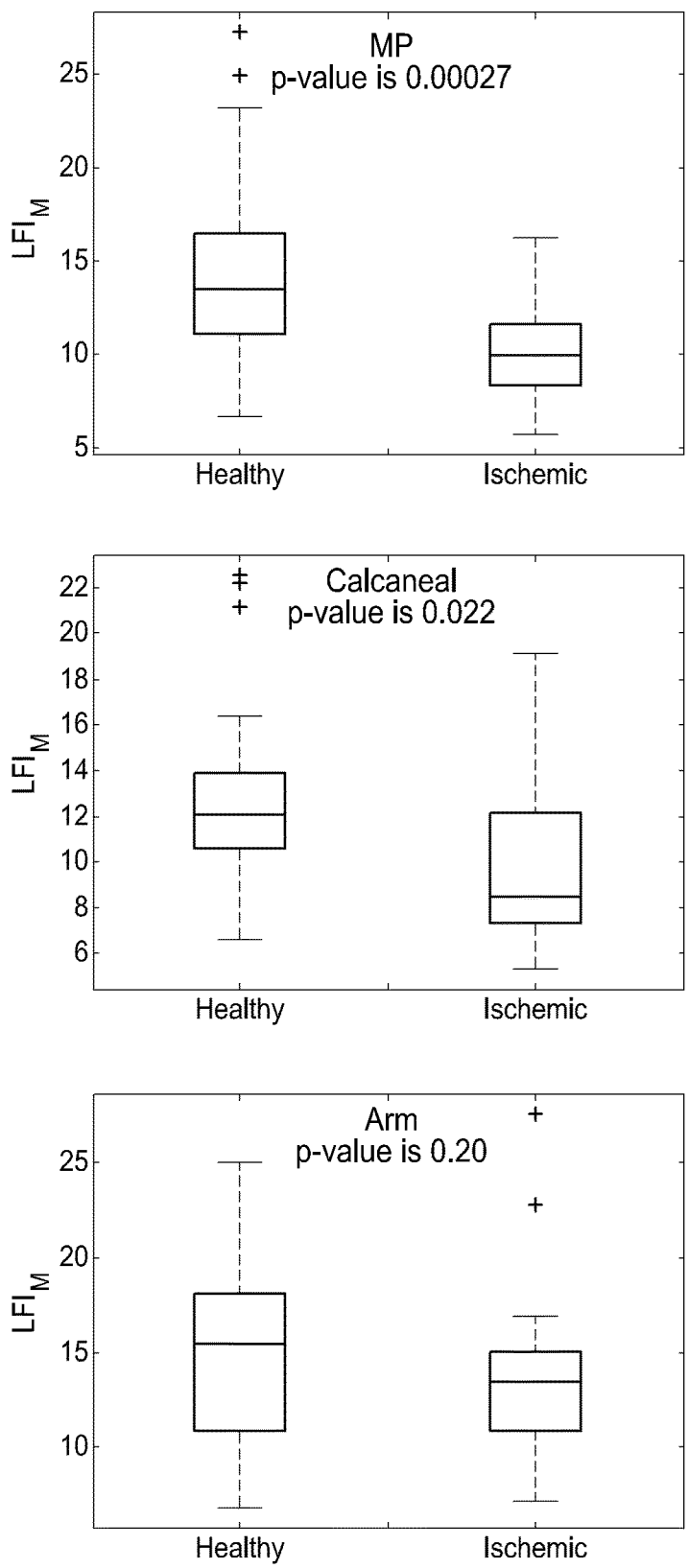

Using the BFI data taken during this study, the $LFI_M$ and $LFI_A$ measurements calculated for each volunteer/patient are shown in FIGS. 9A and 9B, respectively. FIGS. 9A and 9B illustrate boxplots of low frequency oscillation index (LFI) from 26 healthy and 26 ischemic patients, assessed in two different methods: maximum-based ($LFI_M$) in FIG. 9A, and area-based ($LFI_A$) in FIG. 9B. Double sided t-test p-values for medial plantar (MP), calcaneal (C), and deltoid (Arm), respectively, are: 0.00027, 0.022, 0.20 for $LFI_M$, and 0.0015, 0.016, and 0.41 for $LFI_A$. Boxplots are drawn using MatLab, where the horizontal line within the boxes indicates the median value, while the boxes indicate 25 to 75 percentile values, and crosses are outliers.

Receiver operating characteristic (ROC) curves were plotted to assess the diagnostic accuracy of this test in distinguishing ischemic from normal populations. In a ROC curve the true positive rate (Sensitivity) is plotted as a function of the false positive rate (100-Specificity) for different cut-off points. Each point on the ROC curve represents a sensitivity/specificity pair corresponding to a particular decision threshold. One metric used to determine the accuracy of a test is the Area Under the Curve (AUC) of an ROC plot: with an AUC of 0.9 to 1 representing excellent discrimination, while an AUC of 0.5 representing a worthless test. A test with perfect discrimination (no overlap in the two distributions) has a ROC curve that passes through the upper left corner (100% sensitivity, 100% specificity) and an AUC of 1. Therefore, the closer the ROC curve is to the upper left corner, the higher the overall accuracy of the test.

Figure 10B:
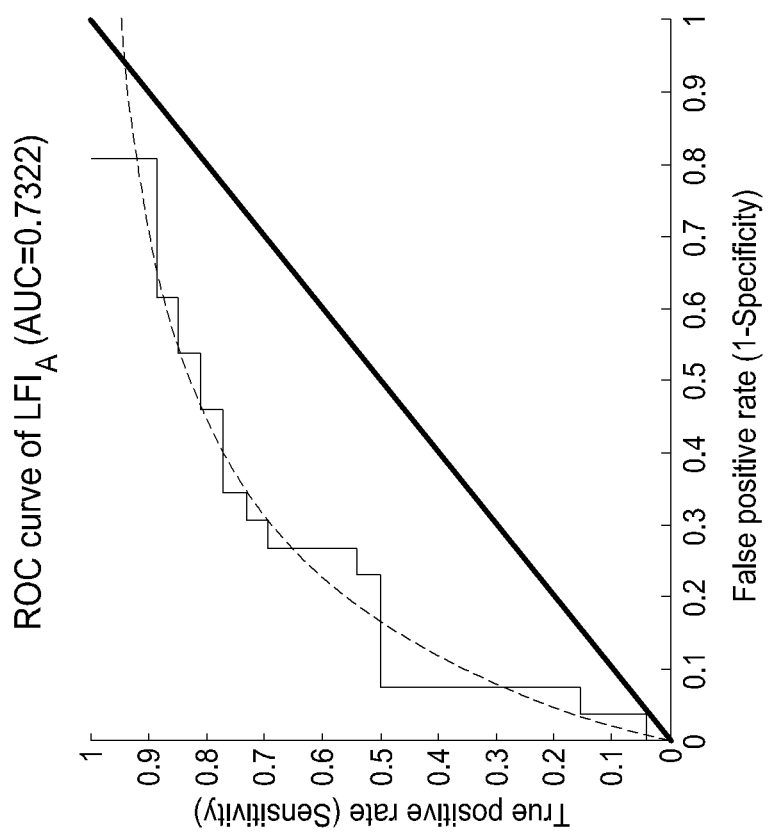
FIGS. 10A and 10B illustrate receiver operating characteristic (ROC) curves for $LFI_M$ and $LFI_A$ respectively measured in the medial plantar (MP) region.
Figure 10A:
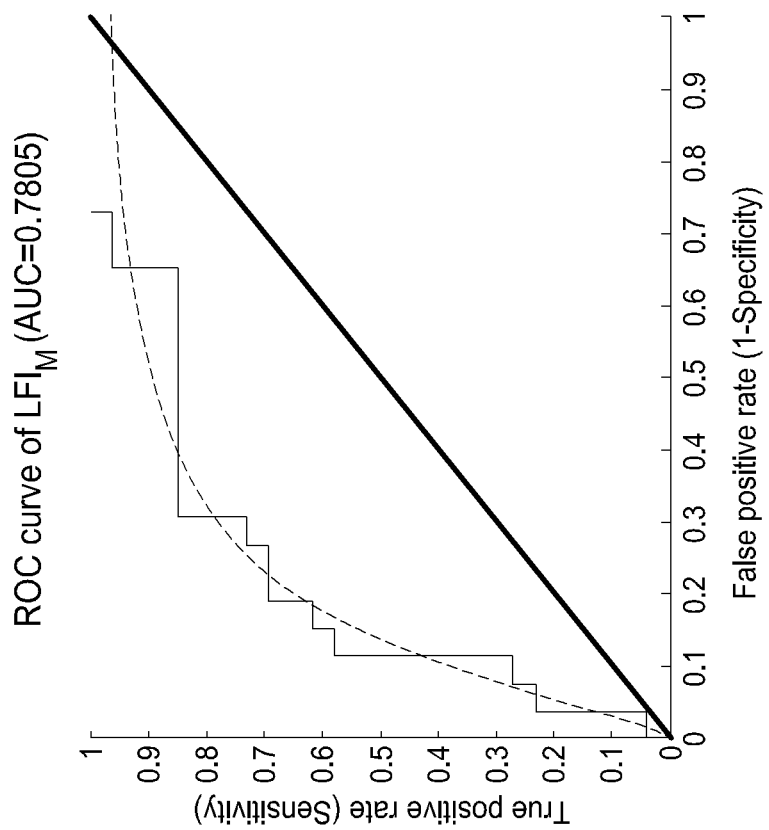

FIGS. 10A and 10B illustrate receiver operating characteristic (ROC) curves for $LFI_M$ and $LFI_A$ respectively measured in the medial plantar (MP) region. Area under the curve (AUC) is 0.7805 and 0.7322 for $LFI_M$ and $LFI_A$, respectively. Dashed curves are results of nonlinear curve fitting.

As MP shows the smallest p-values for both $LFI_M$ and $LFI_A$ cases in FIGS. 9A-9B, MP data were used to draw ROC curves in FIGS. 10A-10B. AUC of the ROC curves of around 0.75 or higher showing a decent discriminating power. By way of comparison, Figoni et al (J. Rehab Res Dev 2006: 43 (7) 891-904) report that $TcPO_2$ has an AUC of 0.82 in discriminating between healthy subjects, and ischemic patients (identified as prospective candidates where unilateral transtibial amputation was imminent or scheduled because of lower-limb ischemia). The ischemic group of patients in the Figoni study however suffered from an extreme degree of ischemia in that the decision for an amputation at a level much above the site of $TcPO_2$ measurement had already been made. The patients in the study described above however were typical patients in an out-patient setting, with none requiring amputations at the time of testing. Despite this difference in the degree of ischemia between subjects in this study and the Figoni study, the AUC is similar between the studies suggesting a much greater ability for LFI to distinguish subtle differences in the degree of ischemia compared to $TcPO_2$.

The data in FIGS. 9A-10B indicate that $LFI_M$ can be superior to $LFI_A$ in some cases in its ability to distinguish ischemic foot tissue from healthy foot tissue, and that the distinction is particularly pronounced when the measurement is taken at the medial plantar area of the foot, where the p-value is statistically significant, and as small as 0.00027, or even less.

The distinction between healthy and ischemic medial plantar tissue is, in some cases, statistically more highly significant when using $LFI_M$ as the relevant index. Not to be limited by theory, a possible explanation for this may lie in the fact that $LFI_M$ provides a more snapshot insight relative to $LFI_A$. In other words, $LFI_M$ is a measure of the maximal amplitude change, and expect healthy vessels with higher elasticity and better rheology of blood flow would be expected to manifest higher $LFI_M$ values. In contrast, the $LFI_A$ is an averaged measure of LFO, meaning that it averages out the multiple oscillatory changes in a vessel into one averaged change represented by the area under the curve. Given that $LFI_A$ is also capable of distinguishing healthy versus ischemic tissue, it is possible that $LFI_A$ does reflect overall functions of elasticity and rheology over a period of time. It may simply be that, for a 5 minute reading such as that used in this study, $LFI_M$ is a more discriminatory index than $LFI_A$. This hypothesis is supported by smaller p-values associated with the use of $LFI_M$ versus $LFI_A$. In some embodiments, longer or shorter reading periods can be utilized, such as about 1, 2, 3, 4, 6, 7, 8, 9, 10, 15, 20, 25, or 30 minutes as non-limiting examples.

This distinction, as shown in FIGS. 9A-9B, in some cases is most clearly seen in the medial plantar, relative to the calcaneal area of the foot, and the deltoid. The medial plantar vasculature depends upon an intact pedal-plantar arch for blood supply, and it is at this level that occlusive arterial disease most commonly presents. The medial plantar is therefore much more vulnerable to ischemia, in contrast with the calcaneal circulation which is dually supplied by the peroneal and the posterior tibial vessels. The deltoid region is much less affected than the feet, if at all, as significant upper limb arterial disease is rare in atherosclerosis and/or diabetes.

In some embodiments, an $LFI_A$ value of less than about 130, 127.5, 125, 122.5, 120, 117.5, 115, 112.5, 110, 107.5, 105, 102.5, 100, 97.5, 95, 92.5, 90, 87.5, 85, 82.5, 80, 77.5, 75, 72.5, 70, 67.5, 65, 62.5, 60, 57.5, 55, 52.5, 50, or less can serve as a pre-determined discriminatory cut-off value between a first population and a second population and indicate a risk factor for a characteristic or a disease characteristic, e.g., ischemia, such as severe ischemia, and notify the clinician by prompting an audible, visual, or other signal, such as visually on the display, for example.

In some embodiments, an $LFI_M$ value of less than about 15, 14.5, 14, 13.5, 13, 12.5, 12, 11.5, 11, 10.5, 10, 9.5, 9, 8.5, 8, 7.5, 7, 6.5, 6, or less can serve as a pre-determined discriminatory cut-off value between a first population and a second population and indicate a risk factor for a characteristic or a disease characteristic, e.g., ischemia, such as severe ischemia, and notify the clinician by prompting an audible, visual, or other signal, such as visually on the display, for example.

Multi-Dimensional Data Analysis of Power Spectrum

In addition to the parameters $LFI_M$ and $LFI_A$ described above, there are other parameters or methods of analyzing the BFI data for the purposes of discriminating between the two patient populations. In some embodiments, multiple independent parameters can be utilized in conjunction in order to more accurately discern to which population a patient belongs.

Analysis of multi-dimensional data sets can be facilitated by the use of various strategies including, but not limited to, the use of artificial neural networks (ANN), extreme learning machines (ELM), and support vector machines (SVM). In particular, an SVM is a means to define a hyperplane in multi-dimensional space that discriminates between two populations. In some embodiments, a SVM can be utilized to process multi-dimensional inputs comprising parameters such as, but not limited to, relative signal powers in specific frequency bands of a particular anatomical BFI signal, absolute signal powers in specific frequency bands of a particular anatomical BFI signal, and/or correlation coefficients between band pass filtered BFI signals.

In some embodiments, an SVM can utilize one, two, or more of the following five independent inputs (as described in Table 1) from each patient from the data set described above: Band pass (0.001 Hz to 0.110 Hz) relative power of the calcaneal BFI; Band pass (0.001 Hz to 0.110 Hz) relative power of the medial plantar BFI; Band pass (0.471 Hz to 0.478 Hz) absolute power of the deltoid BFI; Band pass (0.471 Hz to 0.478 Hz) absolute power of the medial plantar BFI; and/or Band pass (0.341 Hz to 0.351 Hz) correlation coefficient between deltoid and medial plantar BFI.

When run against the same dataset of 26 healthy/26 ischemic patients, the SVM achieved, in one embodiment, an accuracy of 0.961, a sensitivity of 0.961, and a specificity of 0.961. The ROC of this SVM is shown in FIG. 11, which illustrates a ROC curve for a 5-dimensional SVM utilizing patient BFI input parameters as noted in the preceding paragraph.

Figure 12:
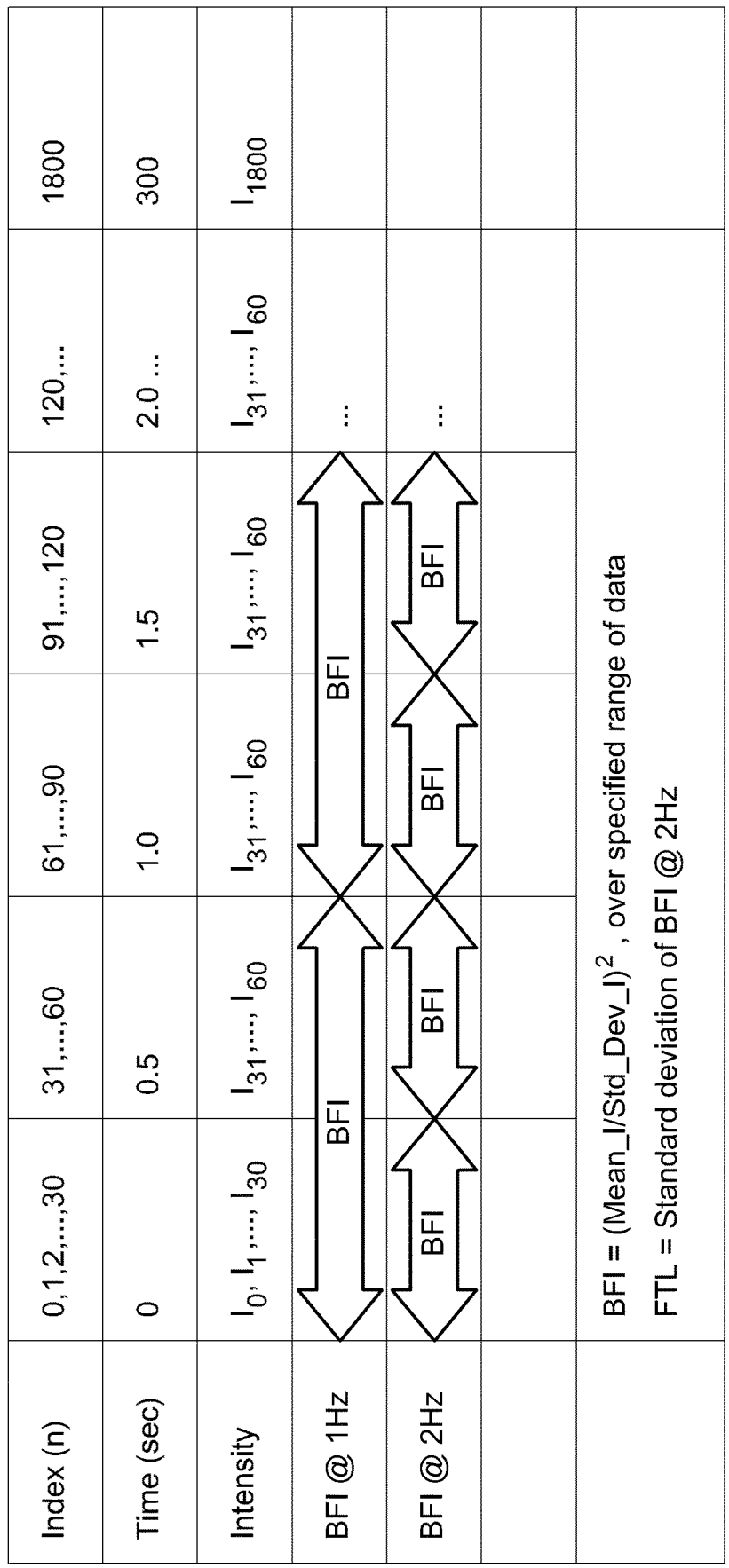
FIG. 12 shows The Flow Transform Level (FTL) relating to the time series BFI, e.g., derivation of FTL from time series DSCA blood flow index (BFI) data, where intensity is measured at a frame rate of 60 Hz.

Statistical Analysis of a BFI Signal:

In some embodiments, the statistical parameters of the BFI signal can also be used as a discriminator. The Flow Transform Level "FTL" is the standard deviation of the BFI signal calculated at 2 Hz. FIG. 12 shows how this is derived from and relates to the time series BFI, e.g., derivation of FTL from time series DSCA blood flow index (BFI) data, where intensity is measured at a frame rate of 60 Hz. Other frame rates, such as 30 Hz for example, can also be utilized depending on the time duration selected.

The standard deviation of 5 minutes of Medial Plantar BFI data sampled at 1 Hz and 2 Hz was calculated, and the resulting ROC curves are shown in FIGS. 13A and 13B. FIG. 13A illustrates the ROC of Standard Deviation of BFI@ 1 Hz; FIG. 13B illustrates the ROC of Standard Deviation of BFI@ 2 Hz. As noted elsewhere herein, the amount of time data sampled can be selected depending on the desired clinical result, such as about 30 seconds, 45 seconds, 1 minute, 75 seconds, 90 seconds, 105 seconds, 2 minutes, 3 minutes, 4 minutes, 5 minutes, or another time interval. Other frequencies other than 1 Hz or 2 Hz can be utilized as well, such as a frequency of between about 0.5 Hz an about 10 Hz, or between about 1 Hz and about 10 Hz.

If the standard deviation of the BFI at 2 Hz is focused on, and the data set shortened and analyzed, a slow degradation of the AUC down to 2 minutes can be observed, and a precipitous drop at 1 minute. This result is shown in Table 2.

TABLE 2

Dependence of FTL AUC on sample time/data set size.

| Sample time | AUC for FTL |
|---|---|
| 5 min | 0.9645 |
| 4 min | 0.9633 |
| 3 min | 0.9554 |
| 2 min | 0.9241 |
| 1 min | 0.7428 |

The Standard Deviation of BFI from calcaneal and arm also shows significant difference between healthy and ischemic patients, but not strongly as with the medial plantar. The p-values of three positions are compared in FIGS. 14A-14C, which are box plots of FTLs in the medial plantar, calcaneal, and arm regions, respectively.

Assessment of Results

An AUC of the ROC curves of around 0.75 or higher showing a decent discriminating power, and an AUC exceeding 0.90 is considered excellent in some embodiments. By way of comparison, Figoni et al (J. Rehab Res Dev 2006: 43 (7) 891-904) report that tcPO2 has an AUC of 0.82 in discriminating between healthy subjects, and ischemic patients (identified as prospective candidates where unilateral transtibial amputation was imminent or scheduled because of lower-limb ischemia). The ischemic group of patients in the Figoni study however suffered from an extreme degree of ischemia in that the decision for an amputation at a level much above the site of TcPO2 measurement had already been made. In some embodiments, patients analyzed are typical patients in an out-patient setting, with none requiring amputations at the time of testing. FIG. 14D illustrates a graph showing FTL values obtained in one study for healthy and ischemic patients on the Y axis and the patient numerical identifier on the X axis.

Despite this difference in the degree of ischemia between subjects with respect to the Figoni study, one-dimensional AUC using $LFI_M$ can be similar to the Figoni study suggesting a much greater ability for LFI to distinguish subtle differences in the degree of ischemia compared to TcPO2. When utilizing multiple parameters in our SVM, an AUC of 0.969 or better can be achieved, far exceeding the performance reported for tcPO2.

Using FTL (Standard Deviation of BFI@ 2 Hz) an AUC of 0.9645 with a single parameter can be achieved from a single sensor located at the medial plantar. This greatly simplifies the measurement in some cases and can increase the utility and ease of implementation of technique for clinical diagnostic and/or screening applications.

In some embodiments, an FTL value of less than about 10, 9.75, 9.5, 9.25, 9, 8.75, 8.5, 8.25, 8, 7.75, 7.5, 7.25, 7, 6.75, 6.5, 6.25, 6, 5.75, 5.5, 5.25, 5, 4.75, 4.5, 4.25, 4, 3.75, 3.5, 3.25, 3, 2.75, 2.5, 2.25, 2, or less can serve as a predetermined discriminatory cut-off value between a first population and a second population and indicate a risk factor for a characteristic or a disease characteristic, e.g., ischemia, such as severe ischemia, and notify the clinician by prompting an audible, visual, or other signal, such as visually on the display, for example.

Referring back to FIGS. 1D-1H, DOF sensors can be separately placed at different topographical regions of the foot, for example the DOF sensors can be placed at each of the pedal angiosomes using separate support structures. In another embodiment, however, a plurality of DOF sensors can be incorporated into a single support structure for simultaneous measurement of different pedal regions, for example the pedal angiosomes. One such embodiment is illustrated in FIGS. 15A-15C. A side-firing DOF sensor is shown in FIG. 15A. As illustrated, light from a source can enter the sensor 602 through input cable 604, and can exit the sensor 602 through the output cable 606 towards the detector. In some embodiments, the input cable and the output cable can be bundled together. Rather than having the cable oriented perpendicular to the surface of the tissue to be measured, in this side-firing sensor the cable is oriented substantially parallel, with an internal prism, mirror, or other optical element redirecting light downwards towards the tissue. As a result, the DOF sensor 602 can be laid flat against the surface of the area to be measured, with the cables 604 and 606 extending substantially parallel to the surface. The overall effect is a more low-profile DOF sensor, with improved comfort, flexibility, and form-factor.

As used herein, the term "sensor" refers to the terminal end of the DOF system that makes contact with the sample, for example the patient's skin. The sensor may include an input optical fiber coupled to a source and an output optical fiber coupled to a detector. In other embodiments, the sensor may comprise receptacles configured to removably receive such optical fibers. The sensor defines the point at which input light is injected into the sample surface and the point at which scattered light is detected from the sample surface. In the illustrated embodiment, the DOF sensor 602 is substantially flat. However, in various embodiments, other shapes are possible. For example, the DOF sensor may be provided with a curved surface, for example contoured to correspond to contours of a patient's body. A DOF sensor may include a concave surface to correspond to the curvature of a wearer's plantar arch, for example. In some embodiments, the DOF sensor can be malleable to permit curvature and flexure to correspond to a patient's body. As noted above, the distance of separation between the source and the detector affects the penetration depth of measured light. More specifically, the significant distance is that between the position on the surface of the tissue at which light is injected, and position on the surface of the tissue at which light is detected. Accordingly, the side-firing DOF sensor 602 may be modified to provide for different penetration depths depending on the part of the body in which blood flow is to be measured. If the DOF sensor is adapted for use in measuring relatively deep blood flow, the source-detector separation can be greater than for a DOF sensor adapted for use in measuring relatively shallow blood flow. In some embodiments, this distance can be variable within an individual DOF sensor. For example, a mechanism may be provided allowing for the source input fiber and/or the detector output fiber to be moved along the length of the DOF sensor to modify the distance therebetween. For example, in some embodiments the source input fiber may be substantially fixed in relation to the sensor, while the detector output fiber is movable. Conversely, in some embodiments the detector output fiber can be substantially fixed in relation to the sensor, while the source input fiber can be movable. In some embodiments, the movable fiber can be slidable along the sensor, with a latch, screw, detent, or other structure provided to releasably fix the location of the movable fiber after a pre-selected distance has been set. In some embodiments, the movable fiber can be mounted onto a support that is threadably mated to a screw, such that rotation of the screw causes the support, and thereby the movable fiber, to be advanced closer to or further from the fixed fiber. Various other configurations are possible. In other embodiments, various optical components within the interior of the DOF sensor can be provided to alter the effective source-detector distance. For example, the positions of the fibers may be fixed, while internal prisms or mirrors or other optical components can be adjusted to direct the light (incident light from the source or scattered light to the detector) to or from different locations.

FIG. 15B illustrates, as one example of a support structure, a cover sock 608 designed to slip over the patient's foot. As shown in FIG. 15C, a plurality of side-firing DOF sensors 602 can be carried by a cover sock. In some embodiments, the side-firing DOF sensors 602 are arranged at positions corresponding to different pedal angiosomes. Since each DOF sensor 602 can be made thin and flexible, they can be sewn or otherwise attached to the cover sock 608 at the appropriate positions. The optical fibers can be bundled and guided outside the foot covering 608 and connected to an analyzer. With this design, applying the multiple DOF sensors to a patient's foot can be quick and essentially foolproof, which is particularly advantageous in the hectic environment of an operating room or catheterization lab.

FIGS. 15D and 15E illustrates another example of a support structure and DOF sensor. As illustrated, the DOF sensor 610 includes bundled wires 612 extending therefrom. The bundled wires 612 include both the input and output optical fibers, as described above. A retention ring 614 is configured to surround the bottom-facing edge of the DOF sensor 610. The retention ring 614 can be affixed to a surface (e.g., a patient's skin) via adhesive pads 616. The adhesive pads 616 can take a variety of forms, including, for example Tegaderm™ Film. In other embodiments, adhesive material is deposited onto the retention rings without the use of separate adhesive pads.

As illustrated, the retention ring 614 can define an aperture configured to receive the DOF sensor 610 therein. In various embodiments, the retention ring 614 can include one or more retention elements configured to releasably mate with corresponding retention elements on the DOF sensor 610. The engagement of corresponding retention elements thereby releasably locks the sensor 610 into position with respect to the retention ring 614. In various embodiments, a latch, screw, detent, or other structure can be provided to releasably fix the DOF sensor 610 to the retention ring 614.

Various other support structures are possible. For example, in some embodiments the DOF sensors may be carried by a series of straps configured to be wrapped around a patient's foot so as to position the DOF sensors appropriately with respect to the desired measurement regions of the pedal topography, for example different pedal angiosomes. In some embodiments, the DOF sensors may be carried by a sheet of flexible material to be wrapped around the patient's foot. In some embodiments, the support structure may be configured to carry one, two, three, four, five, or more DOF sensors. In some embodiments, two or more support structures may be provided for a single patient. For example, a first support structure may carry two DOF sensors and be positioned over a first portion of a patient's foot, while a second support structure may carry two additional DOF sensors and be positioned over a second portion of the patient's foot. In various embodiments, the support structure may be wearable, for example it may be a garment such as a cover sock, shoe, etc. In some embodiments, the support structure can include a strap or series of straps. In other embodiments, the support structure can comprise an adhesive material by which one or more DOF sensors can be attached to a patient's skin. For example, in some embodiments, each of the DOF sensors can be provided with an adhesive on the tissue-facing side so as to ensure that the sensors contact the skin. In some embodiments, mechanical pressure can be applied to the DOF sensors to ensure that they are pressed against the skin—for example an external wrap may be used, or the elasticity of a cover sock or other foot covering may itself be sufficient to ensure that the DOF sensors are adequately held against the skin. In some embodiments, DOF sensors can be embedded into a foot plate sensor such as those used by podiatrists. An individual may step onto the foot plate, and one or more DOF sensors carried by the foot plate can measure absolute and/or relative blood flow at various locations on the foot.

In some embodiments, each DOF sensor may be carried by a different support structure. In other embodiments, a support structure can be configured to carry any number of DOF sensors, for example two, three, four, five, or more. In various embodiments, the support structure can be configured such that, when the support structure is positioned over a patient's foot, the position of the DOF sensors correspond to different topographical locations in the foot including selected pedal angiosomes. The support structure can be configured to carry DOF sensors corresponding to any combination of topographical locations in the foot including pedal angiosomes. For example, in one embodiment a support structure may be configured to carry DOF sensors adapted to measure blood flow at the calcaneal branch of the posterior tibial artery and at the calcaneal branch of the peroneal artery. In another embodiment a support structure can be configured to carry DOF sensors adapted to measure blood flow at the medial plantar artery, the lateral plantar artery, and the calcaneal branch of the posterior tibial artery. Various other configurations are possible, such that the support structure can be tailored to provide DOF sensors at the desired measurement locations.

FIG. 16 is a flow diagram of a method for analyzing relative blood flow. The process 700 begins in block 702 with positioning at least one DOF sensor on a patient's foot at a location corresponding to a pedal angiosome. As noted above, in some embodiments a plurality of such DOF sensors may be positioned at various places on a patient's foot, or other places on the patient's body. In some embodiments, a plurality of such DOF sensors can be used to obtain simultaneous measurements from different topographical locations in the foot including different angiosomes. The process 700 continues in block 704 with obtaining measurement of absolute and/or relative blood flow using the DOF sensor. As noted above, DOF techniques can provide an autocorrelation function indicative of the absolute and/or relative blood flow within the tissue. The process 700 continues in block 706 with signaling the absolute and/or relative blood flow to the operator. For example, the signal may be provided via visual, audible, or tactile communication. In some embodiments, the absolute and/or relative blood flow can be signaled to the operator in substantially real-time, for example within 1 second of measurement. In some embodiments, a display may be provided that shows the autocorrelation functions, a chart of blood flow indices (BFIs), or other indicator of the absolute and/or relative blood flow. Such a display can provide the operator with real-time feedback to guide intra-operative decision-making.

As described above, sensor head designs for DOF sensors traditionally employ fibers with either metal or ceramic ferrules to protect the fiber tip, hence the typical sensor head design is limited to a vertical contact scheme where light out of the fiber is directly coupled into a sample. The vertical fiber design suffers from a number of disadvantages when used in applications for blood perfusion monitoring: it adds bulk, height and positional instability to the sensor head; it may require additional means of support to achieve stable and consistent contact with the skin; and for these reasons, it may cause patient discomfort after prolonged application.

Therefore, it is advantageous to implement a low profile generally horizontal contact sensor head that is both simple and cost-effective. FIGS. 17A-17C illustrate an embodiment of such a DOF sensor head. FIG. 17A illustrates a schematic cross-section of the sensor head 800, and FIGS. 17B and 17C illustrate plan views of two possible embodiments for the sensor head 800. As illustrated, a support structure includes a receptacle member 804 with a groove to receive the optical fibers 806 therein, and a reflector member 808 with a reflecting surface. As illustrated, optical fibers 806 are applied generally horizontally onto the surface of the sample 810, and part of the fiber body is disposed within a groove in a receptacle member 806, and the distal tip of the fiber 806 configured to be positioned between the surface of sample 810 and a reflecting surface of the reflector member 808. Light coming out of the source fiber tip will be reflected off of the reflecting surface in this gap and will be directed towards the sample 810. For the detector fiber, the reverse will happen: only those light paths that fall within the acceptance cone will be reflected off of the reflecting surface and collected by the fiber. In some embodiments, the reflecting surface may comprise a sheet of aluminum foil mounted onto a compliant backing such as a rubber, silicone, or foam pad. It will be appreciated that a wide range of materials may be utilized as reflectors including metal foils, metal films, optically reflective coatings, interference gratings, nano-structured meta-materials, or any other material with suitable optical properties.

When applied to a sample, the planar DOF sensor places the fiber in optical communication with the sample. In some embodiments an optically transparent sterile barrier comprising at least one optically transparent layer may be disposed between the fiber and the sample. The at least one optically transparent layer may be configured to have adhesive coatings to facilitate attachment of the planar DOF sensor onto the surface of the sample/tissue. For example, surgical tape may comprise a support configured to receive the DOF sensor thereon, and to couple the DOF sensor to the sample.

Figure 18B:
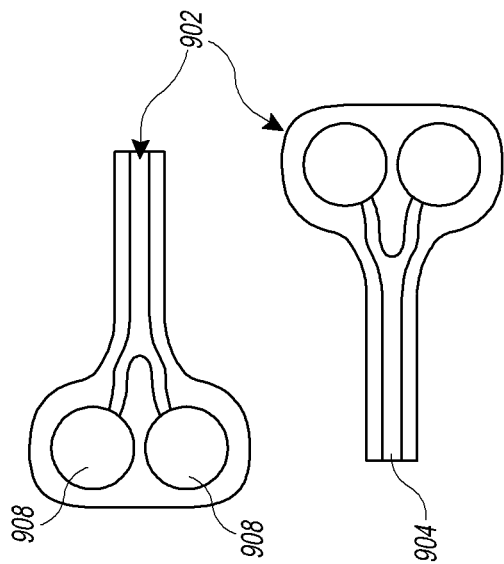
Figure 18A:
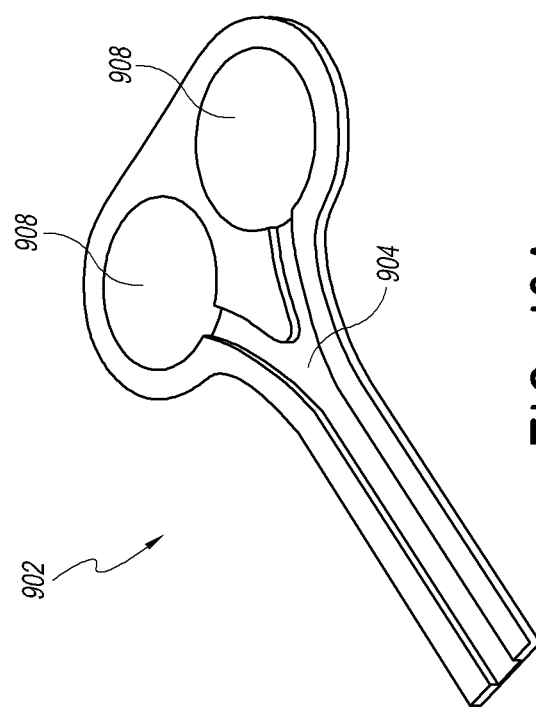
Figure 18C:
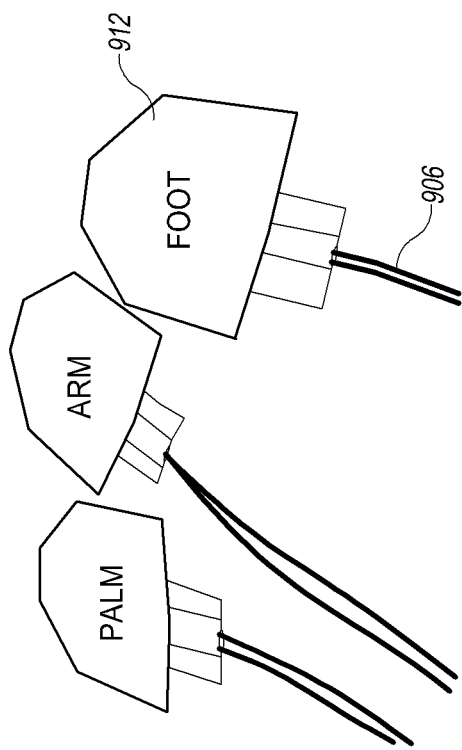
Figure 18D:
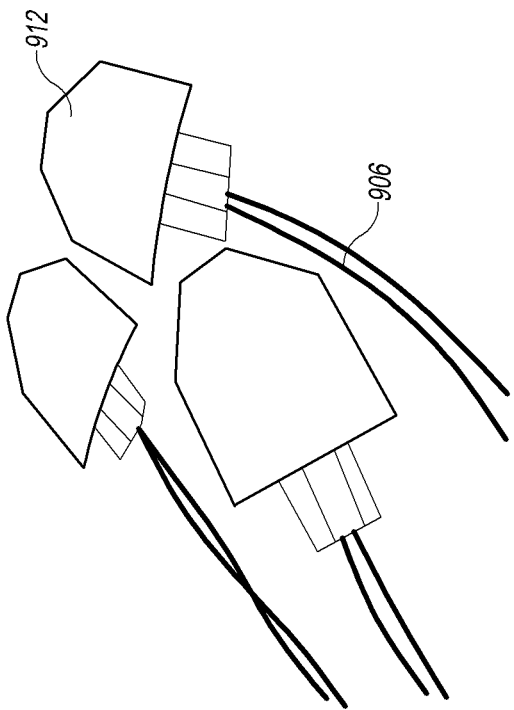

FIGS. 18A-18D show one embodiment of the supports fabricated using 3D printing, with a support comprising an adhesive layer that is disposed between the patient/tissue and the optical fibers. FIGS. 18A and 18B illustrate the support member 902, with FIGS. 18C and 18D showing top and bottom views, respectively, of the sensor heads 900 prepared with a layer of surgical adhesive tape 912 to be disposed between the patient's skin and the fibers. In FIGS. 18C and 18D, the reflector pads 908 and tips of fibers 906 are obscured by the adhesive liner of the surgical tape 912. In other embodiments, the at least one optically transparent layer may not have an adhesive coating, whereupon the planar DOF sensor may be attached to the sample by the application of surgical tape, a mechanical clamp, adjustable strap, or other means.

FIG. 19 illustrates a plurality of DOF sensors 1000 attached to a patient's foot. With a source-detector separation of approximately 1.5 cm on a healthy human foot, arterial cuff occlusion protocol observations display typical blood perfusion variations—e.g., a sudden decrease and plateauing during occlusion, and sharp overshoot and subsequent recovery to baseline value after release of the cuff pressure. FIG. 20 illustrates a DOF sensor attached to a patient's hand. The computer screen indicates a decrease in blood perfusion during arterial cuff occlusion and subsequent reactive hyperemia, indicating healthy blood flow in the hand. In the illustrated graph, two sets of cuff-occlusion are shown with two distinct peaks of reactive hyperemia.

Advantages of the planar DOF sensor head include its low weight, its stability during prolonged application, and a higher level of patient comfort. Its performance is not compromised compared to a vertical sensor head design, and it can be utilized in any optical transmission measurement system in semi-infinite geometry.

Some embodiments may also include memory to store measured or computed data (such as but not limited to BFI, FTI, raw DOF signals), and the capacity to transmit/receive measured or computed data to/from at least one website/database. The at least one website/database can provide patients and clinicians access to the measured or computed data, process/analyze the data and provide notifications to clinicians and/or patients. These notifications may include, but are not limited to, alerts when patient should seek medical attention, updates to clinicians that new patient data is available for review, etc. The data can be stored in a manner and compliant with standards applicable to electronic health records of hospitals and diabetic/podiatry/geriatric/community care centers. Such a system can enable clinicians, care givers, and family members to remotely monitor patients, and can be especially relevant in resource limited regions where access and travel to clinical care centers are limited and/or difficult. By remotely assessing patient's health, it will be possible to improve clinical care by ensuring that only essential travel is undertaken.

In some embodiments, systems and components as described herein can take the form of a computing system that is in communication with one or more computing systems and/or one or more data sources via one or more networks. The computing system may be used to implement one or more of the systems and methods described herein. While various embodiments illustrating computing systems and components are described herein, it is recognized that the functionality provided for in the components and modules (which may also be referred to herein as engines) of computing system may be combined into fewer components and modules or further separated into additional components and modules. For example, a communications engine may include a first module in communication with a diagnostic imaging modality and a second module in communication with a destination modality. Modules can include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Any modules can be executed by one or more CPUs.

A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein can be implemented as software modules, but may be also represented in hardware or firmware. Generally, the modules described herein refer to logical modules that may be combined with other modules or divided into sub-modules despite their physical organization or storage. In addition, all the methods described herein may be executed as instructions on a CPU, and may result in the manipulation or transformation of data.

In some embodiments, hardware components of the system includes a CPU, which may include one, two, or more conventional microprocessors. The system further includes a memory, such as random access memory ("RAM") for temporary storage of information and a read only memory ("ROM") for permanent storage of information, and a mass storage device, such as a hard drive, flash drive, diskette, or optical media storage device. Typically, the modules of the system are connected using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example.

In accordance with some embodiments, systems may be operatively coupled to a destination modality, such as, for example, an electronic medical record ("EMR"). EMRs may be any software or hardware-software system configured to store and provide access to electronic medical data. In accordance with various embodiments, EMRs may be at least one of an electronic medical record, an electronic health record, and the like. In some embodiments, systems and components thereof can be operatively coupled to a destination modality that can be an email or other messaging modality; SAMBA, Windows, or other file sharing modality; FTP or SFTP server modality; a VPN; a printer; and the like.

In accordance with some embodiments a system may comprise one, two, or more software modules, a logic engine, numerous databases and computer networks configured to provide a user with access to various modalities as described herein and/or an EMR. Systems may be configured such that patient data, or no patient data is recorded by the system. While the system may contemplate upgrades or reconfigurations of existing processing systems, changes to existing databases and business information system tools are not necessarily required. Systems may be implemented or integrated into existing healthcare information management systems, such as EMRs, without changes to the EMR system, and may interface with other modalities without changes to the communication system of the modality.

In accordance with some embodiments, systems may be software or hardware-software systems. For example, systems can include a communication engine configured to receive and transmit medical information operatively coupled to an information converter configured to render diagnostic medical information in a suitable format for storage in a patient EMR; a work list engine configured to create a user selectable task list from orders captured at an EMR and selectable by a user at a medical diagnostic modality; and an event log configured with a user selectable record of transactions and/or errors in data transmission and/or data conversion performed by the system.

In accordance with some embodiments, communication engine may be any software or hardware software-system configured to receive and/or transmit data. Communication engine may be configured to transmit and receive data over a variety of network interfaces including wired and wireless networks or a combination thereof, such as via Ethernet, 802.11x, Bluetooth, FireWire, GSM, CDMA, LTE, and the like. Communication engine may also be configured to transmit and/or receive data with file transfer protocols such as TCP/IP, as well as various encryption protocols, such as, for example, WEP, WPA, WPA2, and/or the like.

Furthermore, in some embodiments, a communication engine may be configured as an active or passive module. When communication engine is passive, it may be configured to be discoverable by various elements of a larger healthcare management system. In this way, communication engine may be configured to receive a command or request from a medical diagnostic modality for a user selected patient, such that the communication engine may transmit the request to an EMR, receive the patient data for a specific patient from the EMR, and transfer the patient data from the EMR to the medical diagnostic modality. As such, communication engine is only configured to receive and transmit data. In some embodiments, communication engine is not configured to collect, capture, or mine data from either an EMR or a medical diagnostic modality.

Clinical Applications

Embodiments of Derivative Indices of DSCA provide a direct assessment of microvascular vasomotion in the patient. Endothelial dysfunction caused by diabetes (Kolluru et al in Intl J of Vascular Med 2012) undermines normal vasomotion, leading to delayed vascular re-modeling and wound healing. The Derivative Indices therefore can in some embodiments provide means to better assess the healing capacity of patients (both diabetic and non-diabetic) and hence direct the optimal use of wound care therapy. Additional use for the Derivative Indices could be for screening patients for peripheral vascular disease, determining the efficacy of a revascularization procedure, such as a bypass, stent, graft, angioplasty, or other procedure, either intraoperatively or postoperatively; predicting response to advanced wound therapies such as HBOT, and determining the optimal sites for limb amputation, for example. Other applications of this technique include, for example, the assessment of plastic surgery grafts or flaps for tissue viability. In some embodiments, DOF sensors can be used to assess blood flow in the foot, ankle, calf, thigh, hand, arm, neck, or other anatomical locations. In some embodiments, the DOF sensors can be positioned within the body, for example within natural orifices, such as the esophagus, stomach, small intestine, colon, or uterus for example to assess blood flow. In various such embodiments, DOF sensors can be disposed in accordance with angiosome theory.

Ischemic Foot Screening

One, two, or more of the Derivative Indices may be used as a tool to screen for ischemic feet, particularly for diabetic patients where the presence of neuropathy as part of the diabetic disease progression means that claudication is often not a reliable manifestation of the severity of underlying peripheral arterial disease, e.g., the patient feels no pain due to diabetic neuropathy, rather than because there is no atherosclerotic disease.

As a screening tool should ideally be small, compact, inexpensive, and widely deployable and utilized by staff with minimal training, in some embodiments the system for screening ischemic feet may be implemented using a small, battery powered, portable, blood perfusion monitor console comprising a single sensor that is attached to the patient's foot for measurement duration of, for example, 10 seconds to 10 minutes. The recorded time series blood perfusion can then be processed into a power spectrum via an internal processor. Alternatively, the time series data may be telemetered to a distributed computational network for processing. Results of the calculated one or more Derivative Indices can then be reported directly to the physician's office or care giver for further follow-up. Alternatively, caregivers or clinicians may remotely access results via the internet, smart phone, or other telecommunications device. Patients who present with endothelial dysfunction and/or ischemia can then be referred to primary care centers for more directed evaluation and therapy.

Diabetic feet are also at risk of ulceration from a combination of ischemia, high plantar pressures from bio-mechanical change in the foot as well as neuropathy. In clinical practice, the combination of these three factors leads to a diagnosis of a diabetic foot at risk of ulceration ("DFAR"). Annually, 25% of diabetics are thus diagnosed to be at risk of ulceration, and 50% of such diagnosed patients subsequently undergo a major or minor amputation of foot tissue.

Some approaches measure the three diagnostic indicators separately—the ankle-brachial index ("ABI") can be used to measure ischemia, while a pressure footplate can be used to measure plantar pressure, and a pressure-sensitive monofilament that buckles at a pre-determined pressure but is not felt on application by the patient can be used to diagnose neuropathy. There are multiple disadvantages of these approaches, including (a) ABI measurements are highly variable depending on the procedural protocol that in turn varies from hospital to hospital. The position of the patient is highly material as ankle systolic pressure is affected by posture—1 mmHg higher for each inch the ankle is below the heart; (b) the presence of calcified vessels in diabetic feet can generate falsely high readings of ABI; and (c) the clinic workflow can become congested at the physician's desk as it takes a medically qualified doctor to subjectively interpret on a case-by-case basis three different reports for ischemia, plantar pressure, and neuropathy in order to make a determination of a diabetic foot at risk. It typically takes 30 minutes or more for a physician to run these tests and make a diagnostic determination.

Some embodiments described herein include one, two, or more flow sensors, such as diffuse optical flow (DOF) sensors configured to measure one, two, or more parameters relevant to blood flow, and operably connectable to one, two, or more anatomical regions of interest, such as a foot or hand for example. The sensors are in operative wired or wireless communication with a hardware console unit configured to receive the parameters from the sensors and perform pre-determined calculations as described elsewhere herein. Some embodiments described herein comprise a pressure-sensitive footplate into which is embedded at least one diffuse optical flow (DOF) sensor heads which will be in optical communication with an angiosome or other topographic location of the patient's foot so as to take a measurement based on one or more of the Derivative Indices, and, optionally, at least one DOF reference sensor head that can be applied to a suitable location on the patient such as the thumb or the earlobe, to obtain a reference reading for computation of the FTI. The device may generate a quantitative readout per foot of the absolute BFI and/or FTI and/or any other Derivative Index, as well as the plantar pressure, each with objective threshold criteria for indicating whether a foot needs further physician review and therapeutic or pre-emptive intervention. The device represents a simple, objective and intuitive method of diagnosing a diabetic foot at risk of ulcer in a way that removes inter-operator variation and avoids multiple tests. In some embodiments, to generate a report of the relevant data, the patient merely has to stand on the footplate device for a short period of time, for example approximately 30 seconds with an adhesive sensor head affixed to one thumb or other reference point. Such a simple outpatient tool can be easily used by nurses, clinical technicians, physiotherapists etc. in the diabetes or podiatry care community to more efficiently triage diabetic feet at risk and thereby ease the workflow congestion caused by the chronic shortage of physicians in many aging communities worldwide.

Guiding Wound Management

Current techniques utilized to assess wound healing potential are sub-optimal. $TcPO_2$ measurements have been shown to be poor predictors of HBOT outcome (Fife et al, Wound Rep Reg 2002; 10: 198-207). Skin perfusion pressures are in fact better predictors of wound healing than $TcPO_2$ (Lo et al in Wounds 2009), though with a diagnostic accuracy of less than 80% for an SPP cutoff value of <30 mmHg (Castruonuovo et al in JVS 1997).

It is possible that $TcPO_2$ and SPP will never reach the highest levels of diagnostic accuracy demanded by the clinical community, as both are limited by the fact that measurements are only skin deep. Studies by Rucker et al (Rucker et al in Am J Physiol Heart Circ, 2000) showed that under critical perfusion conditions, it is the vasomotion and flow motion in the skeletal muscle that preserve nutritive function to surrounding tissue like skin, subcutis and periosteum, which are incapable of this protective mechanism. In addition, the impaired endothelial dysfunction as seen in diabetes directly impairs vasomotor function (Kolluru et al in Intl J of Vascular Med 2012) leading to delayed vascular re-modeling and wound healing. It follows therefore that measurement of either just partial pressure of oxygen ($TcPO_2$) or perfusion pressure in the skin alone (SPP) does not reflect the critical nature of the ischemia in the underlying tissue, and hence provides at best a partial indicator/predictor of wound healing.

In contrast, the Derivative Indices directly measure the vasomotor function in tissue at a depth much greater than skin (up to 2 cm), and thus have the potential to be a superior predictor of wound healing, and a powerful tool to guide the appropriate therapy for wound healing. In some embodiments, blood flow can be measured at a depth of greater than about 2 mm, 4 mm, 6 mm, 8 mm, 10 mm, 12 mm, 14 mm, 16 mm, 18 mm, 20 mm, or more.

Conservative therapy for wounds (e.g. bandages, moist dressings) can suffice to facilitate wound healing if the blood perfusion around the wound tissue is not compromised beyond the minimal threshold for passive healing to occur. In cases where the perfusion is thus compromised, however, the inappropriate use of conservative wound therapy causes a time lag between the first presentment of a wound in a clinical setting to an effective therapy commensurate with the seriousness of the wound condition. The TIME (Tissue viability, Infection control, Moisture, Epithelialization) model of wound care emphasizes the need for early diagnosis of tissue viability or otherwise in a wound, which diagnosis will then drive the therapy pathway towards wound healing. The single most important determinant of tissue viability in a wound is its blood supply. The ability to assess the blood perfusion around the wound bed allows clinical decisions to be made regarding either (a) continuation of conservative therapy if tissue is viable or, (b) if blood perfusion is too severely compromised for successful conservative therapy, to progress to more advanced wound care products like chemical debriding agents, or advanced wound therapies such as topical negative pressure, hyperbaric oxygen therapy etc. In more serious cases, the patient can be directed to revascularization by peripheral interventional procedures.

Guiding Amputation Levels

The Derivative Indices may also have a role in predicting the success of amputation healing. Amputation is typically performed on patients with severe limb ischemia who cannot be treated with reconstructive vascular surgery, patients with diabetic foot ulcers or venous ulcerations. Approximately, 85-90% of lower limb amputations in the developed world are caused by peripheral vascular disease and poor wound healing accounts for 70% of the complication cases that arises from amputation. In spite of the use of state of the art technologies to assess amputation level, the healing rate of below-knee amputation ranges between 30 and 92%, with a re-amputation rate of up to 30%. Post-amputation wounds fail to heal if the blood perfusion at the amputation level is inadequate to support wound healing. When this occurs, the surgical wound breaks down, often with superadded infection, and can add to revision amputation where the leg is amputated at a higher level, or to the morbidity of the patient as well delays in patient rehabilitation and prosthetic fitting. The ability to measure blood perfusion using one or more of the Derivative Indices may enable the physician to better predict successful amputation healing at different levels of the leg to be amputated. This will guide the physician via objective criteria as to the appropriate level of amputation to minimize patient pain and suffering while maximizing limb preservation.

Screening for Hyperbaric Oxygen Therapy

Hyperbaric oxygen therapy to aid the healing of chronic non-healing wounds is currently directed by the measurement of $TcPO_2$ in the skin surrounding the wound bed before and after the administration of 100% oxygen. HBOT involves the administering of oxygen at levels 2-2.5 times sea level in a chamber. The administration of HBOT as a therapy over a long period of time is not only expensive and comes with many undesirable side effects such as ear and sinus barotrauma, paranasal sinuses and oxygen toxicity of the central nervous system. (Aviat Space Environ Med. 2000; 71(2):119-24.) Moreover, a retrospective study of 1144 patients (Wound Rep Reg 2002; 10:198-207) indicated that 24.4% of chronic wound patients who received HBOT obtained no benefit from it. There is therefore a need to better predict the success of HBOT for any given individual. Since measurements of the Derivative Indices are taken at tissue depths well below skin level, it holds potential for the ability to identify those patients for whom HBOT may well be unsuitable.

Assessment of Surgical Flaps

A further use of the Derivative Indices in clinical practice lies in surgical procedures, particular in plastic and reconstructive surgery, where pedicled or free tissue flaps are used to cover wound defects. Skin, myocutaneous, fascio-myocutaneous and osseomyocutaneous flaps are used to reconstruct tissue defects that may result from trauma, surgery for tumors, infections or congenital diseases. These flaps depend upon the blood supply from either their own blood vessels or from micro-vascular reconstructions with the blood vessels in the vicinity of the recipient tissue bed for their survival. Both types of flaps (pedicled and free) are crucially dependent on the blood perfusion within them for the flaps to survive. Flap perfusion needs close monitoring especially in the first few hours to days after the reconstruction procedure and early detection of loss of perfusion will help to direct the patient for further surgical procedures as needed to ensure continued flap viability. Monitoring the perfusion of these flaps either via surface sensors or sensors within the flap tissue may guide the physician towards an early intervention that can preserve the viability of the flap.

The Derivative Indices can be potentially used to monitor flap blood perfusion continuously in the post-operative period and prevent flap loss due to delayed detection of flap ischemia.

Intravascular and/or Intra-Luminal Tissue Probes for Use in Guiding Decisions for Various Therapies In another embodiment, a DOF sensor for blood flow assessment, e.g., intravascular use comprises at least two fibers configured to emit/receive optical signals at their distal ends, that is delivered via percutaneous and/or transluminal means into an organ or tissue bed that allows for DCS or DSCA measurements of blood perfusion in tissue volumes which are in optical communication with the at least two fibers. Such an intravascular sensor may be configured to have a small cross-section similar to a guidewire of between about 0.01 to about 0.04 inches (or about 250 microns to about 1 mm). The intravascular sensor may be disposed within a flexible sheath that will protect it during delivery, and facilitate insertion of the probe into the target tissue, whereupon the sheath may be partially retracted or the distal tip of the probe partially extended beyond the end of the sheath, so as to put the distal ends of the at least two fibers in optical communication with the tissue whose perfusion is to be measured.

Intravascular and/or intra-luminal tissue probes can enable the real-time measurement of blood perfusion in visceral organs or tissue to guide decisions in various medical therapies, including current treatment protocols for cancer therapy and vascular malformations. These examples are described in greater detail below. In some embodiments, systems and methods as disclosed herein can be utilized for the diagnosis and assessment of the efficacy of various therapeutic interventions for a wide variety of indications, including transient ischemic attacks and acute ischemic strokes (and the efficacy of a neurointerventional revascularization procedure, such as angioplasty or stent placement), ischemic bowel, pulmonary embolism, myocardial infarction, and others. In some embodiments, systems and methods can also measure active bleeding (such as GI bleeding) and confirming the cessation thereof. Other indications are described below.

(a) Measuring Tumor Vascularity and its Impact on Photodynamic Therapy as Well as Tumor Sensitization Measurements Before Radiofrequency Ablation The following articles refer to the need for assessing tumor blood flow in directing radiotherapy, chemotherapy and photodynamic therapy, and are hereby incorporated by reference in their entireties. (Int. J. Radiation Oncology Biol. Phys 2003 V 55, No 4, pp 1066-1073, "Nitric oxide-mediated increase in tumor blood flow and oxygenation of tumors implanted in muscles stimulated by electric pulses", B. F. Jordan, Bernard Gallez et al; The Oncologist 2008, 13:631-644 "Use of $H_2$ $^{15}$O-PET and DCE-MRI to Measure tumor blood flow", Adrianus J de Langen et al; Radiat Res 2003 October 160 (4) 452-9 "Blood flow dynamics after photodynamic therapy with verteporfin in the RIF-1 tumor" Chen B Poque, et al) In brief, the potential for success for chemotherapy is higher in well-perfused tumors. Prior knowledge of this can be used to identify those patients likely to respond well to treatment and stream such patients with greater confidence for chemotherapy treatment. Quantitative measurement of tumor blood flow may also help calculate doses of chemotherapeutic agents to be delivered, especially when such chemotherapy is directly delivered into the tumor via intra-luminal or endovascular means. This will help to avoid the unnecessary and painful chemotherapy of patients who are unlikely to benefit from treatment due to the poor vascularity of their tumors.

Perfusion has also been shown to play a key role in the success of hyperthermic treatments like radiotherapy and photodynamic therapy. Oxygen deficiency in tumors has been shown to reduce repose to non-surgical treatment modalities like radiotherapy and chemotherapy. This oxygen deficiency may be caused by decreased tumor perfusion (diffusion-related hypoxia) or changes in red cell flux (acute hypoxia). Increasing tumor perfusion by various methods such as use of vasoactive agents, carbogen breathing and electrical stimulation of skeletal muscle surrounding the tumor to increase tumor blood flow have been shown experimentally to have radiosensitizing effects. Photo-dynamic therapy (PDT) uses the principle of light at specific wavelengths causing damage to tumor vasculature and rendering the tumor ischemic, i.e., starving the tumor of its blood supply. Success of PDT is thus assessed by the extent to which this ischemia is achieved. The ability to measure tumor blood flow either by endovascular or intra-luminal means can thus help direct the use of these methods to enhance tumor response or to assess tumor response to these non-surgical therapies.

(b) Intravascular and/or Intra-Tissue Probes to Guide Injection of Sclerosing and Embolic Agents During Treatment of Vascular Malformations Vascular malformations ("VMs"), such as arterio-venous malformations, are a network of abnormal small vessels that are formed spontaneously or occur congenitally or following trauma to create an alternate conduit of blood flow between arteries, veins and capillaries, bypassing the normal blood flow that originates from the artery through the capillary bed of an organ or tissue and thence into the vein. Clinical indications for treatment of a VM include local symptoms of pain, bleeding or ulceration at the site of the VM, and significant cardiac strain (including high output cardiac failure) from the high volumes of blood that flow within these lesions. Superficial VMs may need treatment for cosmetic reasons as well.

The treatment for VMs comprises injection via an endovascular micro-catheter of a sclerosing agent such as absolute alcohol or sodium tetradecylsulphate, which are toxic to blood vessels and cause sclerosis or scarring that closes up the small vessels within the VM. This may be the sole procedure or as part of a surgical procedure wherein the volume of blood flowing within the VM is reduced prior to surgical excision. Caution is required during this procedure because excessive injection of the sclerosing agent can lead to overflow into normal blood vessels, resulting in significant damage such as skin necrosis, limb loss, acute pulmonary hypertension, or even death. The challenge for the physician is that a balance must be struck between injecting enough sclerosing agent to completely close up the VM, but not so much that the sclerosing agent leaks out and causes serious damage elsewhere. Real-time perfusion monitoring of the VM can signal when blood flow has ceased within the VM or reduced sufficiently to allow surgical resection without significant loss of blood. This may instruct the physician that enough sclerosing agent has been injected and to avoid further injection, thereby reducing the risk of an adverse outcome.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "discriminating between two populations" includes "instructing the discriminating between two populations." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system to determine whether a patient is within a first healthy patient population or a second ischemic patient population, the system comprising:

a processor configured to receive blood perfusion measurements associated with the patient as a function of time to obtain time series data for between 30 seconds and 10 minutes using diffuse speckle contrast analysis (DSCA) to determine a blood flow index signal; calculate a standard deviation from the blood flow index signal sampled at a frequency of 2 Hz to determine a Flow Transform Level measurement; use the at least one Flow Transform Level measurement to determine whether the patient is within the first healthy patient population or the second ischemic patient population, and generate an indicator in response to determining whether the patient is within the first healthy patient population or the second ischemic patient population;

at least one diffuse optical flow sensor configured to generate the blood perfusion measurements as a function of time, the sensor configured to send the blood perfusion measurements to the processor;

the sensor comprising an input optical fiber coupled to a source and an output optical fiber coupled to a detector, the sensor configured to be in contact with a skin surface of the patient; and a display configured to display the indicator to a clinician during a medical procedure.

2. The system of claim 1, wherein the time series is between 30 seconds and 5 minutes.

3. The system of claim 1, wherein the discriminator is a Flow Transform Level measurement of less than 10.

4. A method to determine whether a patient is within a first healthy patient population or a second ischemic patient population, the method comprising:
- generating time series data of blood perfusion measurements as a function of time for between 30 seconds and 10 minutes using at least one diffuse optical flow sensor, the sensor in optical communication with a skin surface of the patient and comprising an input optical fiber coupled to a source and an output optical fiber coupled to a detector;
- determining, with a processor, a blood flow index signal using the blood perfusion measurements and diffuse speckle contrast analysis (DSCA);
- calculating, with the processor, a standard deviation from the blood flow index signal sampled at a frequency of 2 Hz to determine a Flow Transform Level measurement;
- using the at least one Flow Transform Level measurement to determine, with the processor, whether the patient is within the healthy first population or the second ischemic population;
- generating, with the processor, an indicator in response to determining whether the patient is within the first healthy population or the second ischemic population; and
- displaying the indicator on a display during a medical procedure.

5. The method of claim 4, wherein the time series is between 30 seconds and 5 minutes.

6. The method of claim 4, wherein the discriminator is a Flow Transform Level measurement of less than 10.

* * * * *